(12) United States Patent
Rowe

(10) Patent No.: US 7,825,217 B2
(45) Date of Patent: Nov. 2, 2010

(54) POLYPEPTIDES FOR BONE MINERALIZATION

(75) Inventor: Peter S. N. Rowe, Prairie Village, KS (US)

(73) Assignee: University of Kansas Medical Center, Kansas City, KS (US)

( * ) Notice: Subject to any disclaimer, the term of this patent is extended or adjusted under 35 U.S.C. 154(b) by 666 days.

(21) Appl. No.: 11/521,684

(22) Filed: Sep. 15, 2006

(65) Prior Publication Data

US 2008/0076717 A1    Mar. 27, 2008

(51) Int. Cl.
*A61K 38/00* (2006.01)
(52) U.S. Cl. .................................................. 530/324
(58) Field of Classification Search ........................ None
See application file for complete search history.

(56) References Cited

U.S. PATENT DOCUMENTS

| 6,673,900 B2 | 1/2004 | Rowe |
| 6,818,745 B1 | 11/2004 | Rowe |
| 2003/0064498 A1 | 4/2003 | Rowe |

FOREIGN PATENT DOCUMENTS

WO    WO 2005/103263    11/2005

OTHER PUBLICATIONS

Rowe et al., *Distribution of mutations in the Pex gene in families with X-linked hypophosphataemic rickets (HYP)*, Human Molecular Genetics 6, 539-549 (1997).
Rowe et al., *MEPE, a New Gene Expressed in Bone Marrow and Tumors Causing Osteomalacia*, Genomics 67, 54-68 (2000).
Dubois et al., *Role of abnormal neutral endopeptidase-like activities in Hyp mouse bone cells in renal phosphate transport*, Am. J. Physiol. Cell Physiol. 283, 1414-1421 (2002).
Matsumoto et al., *Role of cathepsin D in Hyp mouse bone defect*, J. Am. Soc. Nephrol. 14 (2003) [abstract only].
Rowe, *The Wrickkened Pathways of FGF23, MEPE and PHEX*, Crit. Rev. Oral Biol. Med. 15, 264-281 (2004).
Rowe et al., *MEPE has the properties of an osteoblastic phosphatonin and minhibin*, Bone 34, 303-319 (2004).
Bresler et al., *Serum MEPE-ASARM-peptides are elevated in X-linked rickets (HYP) : implications for phosphaturia and rickets*, Journal of Endocrinology 183, R1-R9 (2004).
Rowe et al., *Surface plasmon resonance (SPR) confirms that MEPE binds to PHEX via the MEPE-ASARM motif: a model for impaired mineralization in X-linked rickets (HYP)*, Bone 36, 33-46 (2004).
Rowe et al., *MEPE-ASARM-Peptide Associated Mineralization Defects in X-Linked Hypophosphatemic Rickets (hyp) Is Corrected by Protease-Inhibitors*, ASBMR 27th Annual Meeting Sep. 2005 [abstract only].

*Primary Examiner*—Cecilia Tsang
*Assistant Examiner*—Thomas S Heard
(74) *Attorney, Agent, or Firm*—Stinson Morrison Hecker LLP

(57) ABSTRACT

Polypeptides for improving bone mineralization and/or phosphate update are provided. The peptides include a PHEX zinc binding domain and two ASARM binding domains.

5 Claims, 7 Drawing Sheets

POLYPEPTIDES FOR BONE MINERALIZATION

STATEMENT REGARDING FEDERALLY SPONSORED RESEARCH OR DEVELOPMENT

This invention was made with Government support under Grant No. 7R01AR051598-03, awarded by the National Institute of Health, National Institute of Arthritis and Musculoskeletal and Skin Diseases and Grant No. 7R03DE015900-03, awarded by the National Institute of Health, National Institute of Dental and Craniofacial Research. The Government has certain rights in this invention.

CROSS-REFERENCE TO RELATED APPLICATIONS

Not applicable.

BACKGROUND OF THE INVENTION

1. Field of the Invention

The present invention relates to novel polypeptides useful for treating hypomineralization defects of bone and teeth, such as that leading to rickets, osteomalacia, age-related bone-mineral loss disorders, and osteoporosis.

2. Description of Related Art

PHEX (an acronym for phosphate-regulating gene with homologies to endopeptidases on the X-chromosome) is predominantly expressed in osteoblasts, osteocytes, and odontoblasts. PHEX is a zinc metalloendopeptidase integral membrane glycoprotein having a short cytoplasmic N-terminal region, a single small hydrophobic transmembrane domain, and a large extracellular C-terminal region with a zinc-binding motif having the sequence HEFTH (SEQ. ID NO. 1). Defects in the PHEX gene are primarily responsible for X-linked hypophosphatemic rickets ("HYP"). The disease is characterized by low serum phosphorus, dis-regulated or inappropriately normal serum 1,25 vitamin D3, elevated serum alkaline phosphatase and severe hypomineralization defects of bone and teeth leading to rickets and osteomalacia.

PHEX contains key residues for catalytic activity of small peptides, but the substrate for its oligopeptidase activity remains to be identified. As discussed more fully below, PHEX also functions as protein ligand, most notably for Matrix extracellular phosphoglycoprotein ("MEPE") and a protease-resistant MEPE-derived peptide known as the ASARM peptide.

MEPE belongs to a distinct family of bone-dentin salivary proteins that have recently been named short integrin binding ligand interacting glycoproteins ("SIBLINGS"). Evidence suggests that MEPE inhibits phosphate uptake and mineralization in-vivo and in-vitro and is involved in extracellular matrix mineralization (minhibin). See Dobbie et al., *Infusion of the bone-derived protein MEPE causes phosphaturia in rats* (Abstract), J. Am. Soc. Nephrol. 14:468A (2003); Rowe et al., *MEPE has the properties of an osteoblastic Phosphatonin and Minhibin*, Bone 34:303-319 (2004). For example, MEPE-mediated in vivo phosphaturia in rodents can be induced via bolus administration or infusion. Further, MEPE null-mutant mice have increased bone mass, resistance to aging associated trabecular bone loss, increased mineralization-opposition rate ("MAR"), and a dramatically accelerated mineralization rate in ex vivo osteoblast cultures. See Gowen et al., *Targeted Disruption of the Osteoblast/Osteocyte Factor 45 Gene (OF45) Results in Increased Bone Formation and Bone Mass*, J. Biol. Chem. 278:1998-2007 (2003).

Recent work has shown that MEPE binds to PHEX via the PHEX zinc-binding motif and a carboxy-terminal MEPE motif known as the acidic-serine-aspartate-rich MEPE associated motif ("ASARM"). See Rowe et al., *Surface Plasmon Resonance (SPR) confirms MEPE binds to PHEX via the MEPE-ASARM-motif: A model for impaired mineralization in X-linked rickets (HYP)*, Bone 36:33-46 (2005). Cleavage by the protease cathespin-B, which is expressed in osteoblasts, results in the release of the ASARM peptide. When liberated as a phosphorylated peptide (2.2 kDa) in its free form, this small, acidic, highly charged ASARM peptide is a potent inhibitor of mineralization and phosphate uptake. See Bresler et al., *Serum MEPE-ASARM peptides are elevated in X-linked rickets (HYP): implications for phosphaturia and rickets*, J. Endocrinol. 183:R1-9 (2004); Dobbie et al., *Infusion of the bone-derived protein MEPE causes phosphaturia in rats (Abstract)*, J. Am. Soc. Nephrol. 14:468A (2003). As evidence, researchers have shown excess circulating levels of either COOH-terminal MEPE or ASARM-peptides present in HYP and oncogenic hypophosphatemic osteomalacia ("OHO") patients. See Bresler et al., *Serum MEPE-ASARM peptides are elevated in X-linked rickets (HYP): implications for phosphaturia and rickets*, J. Endocrinol. 183:R1-9 (2004); de Beur et al., *Matrix Extracelluler Phosphoglycoprotein (MEPE), fragments circulate in excess in patients with Tumor-induced Osteomalacia (TIO) and X-linked Hypophosphatemic Rickets (XLH)*, J. Bone Miner. Res. 19:F479 (Abstract) S101 (2004). It has also been confirmed that HYP-mice kidneys have excess levels of ASARM-peptide epitopes in regions consistent with the proximal convoluted tubules. See Bresler et al., *Serum MEPE-ASARM peptides are elevated in X-linked rickets (HYP): implications for phosphaturia and rickets*, J. Endocrinol. 183:R1-9 (2004).

The ASARM cleavage site of MEPE is highly conserved in all cloned species (mouse, rat, monkey, and human), and the ASARM peptide is also extraordinarily resistant to a vast array of proteases, including carboxypeptidases (B/T), cathespins-(BDGK), trypsin, granzyme A, papain, pepsin, kallikrein, plasmin, nardilysin, NEP, and ECEL1/DINE.

Researchers have recently theorized that PHEX protects MEPE from cathepsin proteolysis. See Rowe, *The wrickkened-pathways of FGF23, MEPE and PHEX*, Crit. Rev. Oral Biol. Med 15:264-281 (2004). It has been theorized that the MEPE-PHEX interaction in vivo may therefore prevent proteolytic release of the protease-resistant ASARM peptide by protecting MEPE from cathepsin-B and general protease degradation. See Rowe, *The wrickkened-pathways of FGF23, MEPE and PHEX*, Crit. Rev. Oral Biol. Med 15:264-281 (2004). A summary of the proposed PHEX-MEPE-ASARM-cathepsin pathway is illustrated in FIG. 1.

Both the PHEX gene and MEPE have been cloned, and their sequence disclosed. See GenBank CAA712528; Rowe et al., *Distribution of mutations in the PEX gene in families with X-linked hypophosphatemic rickets (HYP)*, Human Mole. Gen., 6, 539-549 (1997); Francis et al., *Genomic organization of the human PEX gene mutated in X-linked dominant hypophosphatemic rickets*, Gen. Res. 7(6):573-585 (1997); Rowe et al., *MEPE, a new gene expressed in bone-marrow and tumours causing osteomalacia*, Genomics. 67 (1):54-68 (2000); Argiro et al., *Mepe, the gene encoding a tumorsecreted protein in oncogenic hypophosphatemic osteomalacia, is expressed in bone*, Genomics 74:342-51 (2001); Petersen et al., *Identification of osteoblast/osteocyte factor 45 (OF45), a bone-specific cDNA encoding an RGD containing protein that is highly expressed in osteoblasts and osteocytes*, J. Biol. Chem. 275.36172-80 (2000); Rowe, U.S. Pat. No. 6,673,900 entitled "Polypeptide hormone-phosphatonin"; Crine et al., U.S. Pat. No. 6,790,649 entitled "Composition Methods and Reagents for the Synthesis of a Soluble Form of Human PHEX." MEPE maps to 4q21 and shares many features with the SIBLINGS, including RGD motifs, protein glycosylation, phosphorylated residues, similar genomic structures, and the ASARM motif.

The present invention is directed to compositions and methods for promoting bone mineralization and phosphate uptake by targeting a specific event in the PHEX-MEPE-ASARM-protease pathway. In particular, novel ASARM binding compounds are provided. These ASARM binding compounds are polypeptides that mimic key binding residues of the PHEX protein capable of binding to the full-length MEPE or the ASARM fragment, thus reducing the concentration of biologically active ASARM peptides in vivo and in vitro and/or protecting MEPE from proteolysis and release of free ASARM-peptide.

Administration of these novel polypeptides results in improved bone mineralization and renal phosphate uptake.

BRIEF SUMMARY OF THE INVENTION

The present invention is directed to novel polypeptides derived from the PHEX and capable of binding to ASARM. The polypeptides comprise a concatenate of an NH-binding domain linked to a PHEX zinc binding domain linked to a COOH-ASARM domain. The preferred peptides are about 40 to 60 amino acids in length and are capable of binding the phosphorylated and non-phosphorylated ASARM motif in both the free catalytically cleaved ASARM peptide and in full-length MEPE. A most preferred polypeptide is known as SPR4.

Additional aspects of the invention, together with the advantages and novel features appurtenant thereto, will be set forth in part in the description that follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
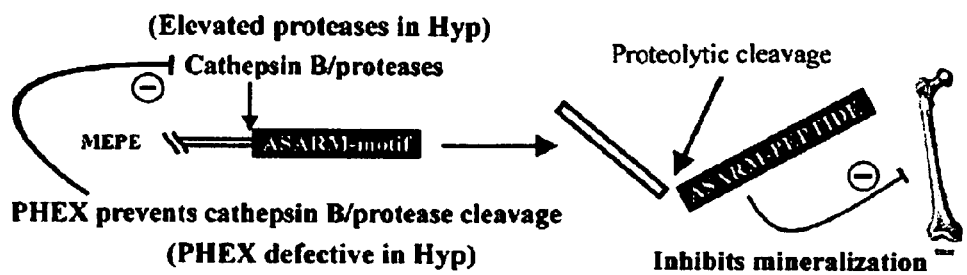
FIG. 1 illustrates the proposed mechanism between PHEX with the ASARM of MEPE to prevent cleavage of the MEPE to release the ASARM peptide.

All patent applications, patents, and publications cited in this specification are hereby incorporated by reference in their entirety. In the case of inconsistencies, the present disclosure, including definitions, will prevail.

The present invention is directed to novel polypeptides capable of interacting and modulating the activity of free ASARM peptide or the ASARM motif in full-length MEPE. In one aspect, the novel polypeptides bind to the ASARM peptide and have an inhibitory effect on the ASARM peptide's deleterious role in bone mineralization and/or phosphate uptake. In another aspect, the present invention is directed to a pharmaceutical composition comprising an effective amount of the novel polypeptides of the present invention together with a pharmaceutically acceptable carrier. In another aspect, the present invention is directed to modulating PHEX activity by use of the peptides of the present inventions as PHEX substrate and/or ligand competition.

As used herein, the term "ASARM" refers to the acidic serine-aspartate-rich associated motif located in MEPE. This region of MEPE contains a recurring series of aspartate and serine residues (SEQ. ID NO. 2; DDSSESSDSGSSSESD). The (D)SSES/E sequence is thought to be a key inhibitor of hydroxyapatite crystal formation and mineralization in salivary statherin. While present at the c-terminus of MEPE, the ASARM is present in other SIBLINGS proteins, most notably in a repeat nature in dentin sialo-phosphoprotein ("DSSP").

As used herein, an "effective amount" of the polypeptides of the present invention is an amount that is sufficient to ameliorate, or in some manner reduce a symptom or effect or stop or reverse progression of a condition associated with ASARM-containing peptides (e.g., HYP, OHO) or by directly modulating PHEX protein activity by substrate competition. Such amount may be administered as a single dosage or may be administered according to a regimen, whereby it is effective.

As used herein, "amelioration" of the symptoms of a particular disorder by administration of a particular polypeptide of the present invention refers to any lessening, whether permanent or temporary, lasting or transient that can be attributed to or associated with administration of the composition.

As used herein, "isolated" refers to material removed from its original environment (e.g., the natural environment if it is naturally occurring), and thus is altered "by the hand of man" from its natural state.

As used herein, a "conservative substitution" in the context of the polypeptides of the present invention is one in which an amino acid is substituted for another amino acid that has similar properties, such that one skilled in the art of peptide chemistry would expect the secondary structure and hydropathic nature of the polypeptide to be substantially unchanged. Further, in the context of the present invention, a conservative substitution is one that does not alter the activity (i.e., the ability of the polypeptide to interact with and modulate the ASARM) of the molecule. Conservative substitutions are likely to be phenotypically silent. Amino acid substitutions may generally be made on the basis of similarity on charge, solubility, hydrophobicity, hydrophilicity, and polarity of the residues.

Thus, the compounds that are encompassed within the scope of the invention are partially defined in terms of amino acid residues of designated classes. The amino acids may be generally categorized into two main classes: hydrophilic amino acids and hydrophobic amino acids, depending primarily on the characteristics of the amino acid side chain. These main classes may be further divided into subcategories that more distinctly define the characteristics of the amino acid side chains. For example, hydrophilic amino acids generally include amino acids having acidic, basic or polar side chains; and hydrophobic amino acids generally include amino acids having aromatic or non-polar side chains. Non-polar amino acids may be further subdivided to include, among others, aliphatic amino acids. The definitions of the classes of amino acids as used herein are as follows:

As used herein, a "hydrophilic" amino acid refers to an amino acid exhibiting a hydrophilicity of less than zero according to the normalized consensus hydrophobicity scale of Eisenberg et al. (J. Mol. Biol. 179: 125-142 (1984)). Examples include arginine (R), aspargine (N), aspartic acid (D), glutamine (Q), glutamic acid (E), histidine (H), lysine (K), serine (S), and threonine (T).

As used herein, a "hydrophobic" amino acid refers to an amino acid exhibiting a hydrophobicity of greater than zero according to the normalized consensus hydrophobicity scale of Eisenberg et al. (J. Mol. Biol. 179: 125-142 (1984)). Examples include alanine (A), cysteine (C), glycine (G), isoleucine (I), leucine (L), methionine (M), phenylalanine (F), proline (P), tryptophan (W), tyrosine (Y), and valine (V).

As used herein, a "negatively charged" or "acidic" amino acid refers to a hydrophilic amino acid having a side chain pK value of less than 7. Acidic amino acids typically have negatively charged side chains at physiological pH due to loss of a hydrogen ion. Examples include aspartic acid (D) and glutamic acid (E).

As used herein, a "positively charged" or "basic" amino acid refers to a hydrophilic amino acid having a side chain pK value of greater than 7. Basic amino acids typically have positively charged side chains at physiological pH due to association with hydronium ion. Examples of genetically encoded basic amino acids include lysine (K), arginine (R), or histidine (H). Examples of non-genetically encoded basic amino acids include the non-cyclic amino acids ornithine, 2,3-diaminopropionic acid, 2,4-diaminobutyric acid, and homoarginine.

As used herein, a "non-polar" amino acid refers to an amino acid having a side chain that is uncharged at physiological pH and which has bonds in which the pair of electrons shared in common by two atoms is generally held equally by each of the two atoms (i.e., the side chain is not polar). Examples of genetically encoded non-polar amino acids include alanine (A), glycine, (G), isoleucine (I), leucine (L), methionine (M), phenylalanine (F), proline (P), and valine (V). Examples of non-encoded non-polar amino acids include Cha.

As used herein, a "polar" amino acid refers to an amino acid having a side chain that is uncharged at physiological pH, but which has one bond in which the pair of electrons shared in common by two atoms is held more closely by one of the atoms. Examples of genetically encoded polar amino acids include serine (S), threonine (T), asparagine (N), glutamine (Q), histidine (H), and tyrosine (Y). Examples of non-genetically encoded polar amino acids include citrulline, N-acetyl lysine, and methionine sulfoxide.

As used herein, an "aromatic" amino acid refers to one having a side chain containing at least one aromatic or heteroaromatic ring. The aromatic or heteroaromatic ring may contain one or more substitutents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently alkyl, alkenyl, alkynyl, aryl, alkaryl, heteroaryl. Examples of genetically encoded aromatic amino acids include phenylalanine (F), tryptophan (W), and tyrosine (Y). Commonly encountered non-genetically encoded aromatic amino acids include phenylglycine, 2-naphthylalanine, β-2-thienylalanine, 1,2,3,4-tetrahydroisoquinoline-3-carboxylic acid, 4-chloro-phenylalanine, 2-fluorophenylalanine, 3-fluorophenylalanine, and 4-fluorophenylalanine.

As used herein, an "aliphatic" amino acids refers to a hydrophobic amino acid having an aliphatic hydrocarbon side chain. Examples of genetically encoded aliphatic amino acids include alanine (A), leucine (L), valine (V), and isoleucine (I). Examples of non-encoded aliphatic amino acids include Nle.

As used herein, a "hydroxyl" amino acid refers to a polar amino acid that contains an —OH moiety. Examples of genetically encoded hydroxylamino acids include serine (S), threonine (T), and tyrosine (Y).

The amino acid residue cysteine (C) is unusual in that it can form disulfide bridges with other Cys residues or other sulfanyl-containing amino acids. The ability of Cys residues (and other amino acids with —SH containing side chains) to exist in a peptide in either the reduced free —SH or oxidized disulfide-bridged form affects whether Cys residues contribute net hydrophilic or hydrophobic character to a peptide. While Cys exhibits hydrophobicity of 0.29 according to the normalized consensus scale of Eisenberg et al., it is understood that Cys is classified as a polar hydrophilic amino acid for the purpose of the present invention. Typically, cysteine-like amino acids generally have a side chain containing at least one thiol (SH) group. Examples of genetically encoded cysteine-like amino acids include Cys. Examples of non-genetically encoded cysteine-like amino acids include homocysteine and penicillamine.

As will be appreciated by those having skill in the art, the above classification are not absolute such that several amino acids may exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has non-polar character. Thus, while not strictly classified as a hydrophobic or non-polar amino acid, in many instances cysteine can be used to confer hydrophobicity to a peptide.

The polypeptides described herein can contain any naturally-occurring (i.e. genetically encoded) or non-naturally-occurring amino acids, including the L-form or D-form of the amino acids, amino acid derivatives as long as the desired function and activity of the polypeptide is maintained. Conventional amino acids include alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Additional amino acids that may be included in the polypeptides of the present invention include: Nle=L-norleucine; Aabu=aminobutyric acid; Hphe=L-homophenylalanine; Nva=L-norvaline; Dala=D-alanine; Dcys=D-cysteine; Dasp=D-aspartic acid; Dglu=D-glutamic acid; Dphe=D-phenylalanine; Dhis=D-histidine; Dile=D-isoleucine; Dlys=D-lysine; Dleu=D-leucine; Dmet=D-methionine; Dasn=D-asparagine; Dpro=D-proline; Dgln=D-glutamine; Darg=D-arginine; Dser=D-serine; Dthr=D-threonine; Dval=D-valine; Dtrp=D-tryptophan; Dtyr=D-tyrosine; Dorn=D-ornithine; Aib=aminoisobutyric acid; Etg=L-ethylglycine; Tbug=L-t-butylglycine; Pen=penicillamine; Anap=1-naphthylalanine; Chexa=cyclohexylalanine; Cpen=cyclopentylalanine; Cpro=aminocyclopropane carboxylate; Norb=aminonorbornylcarboxylate; Mala=L-alpha-methylalamine; Mcys=L-alpha-methylcysteine; Masp=L-alpha-methylaspartic acid; Mglu=L-alpha-methylglutamic acid; Mphe=L-alpha-methylphenylalanine; Mhis=1 alpha-methylhistidine; Mile=L-alpha-methylisoleucine; Mlys=L-alpha-methyllysine; Mleu=L-alpha-methylleucine; Mmet=L-alpha-methylmethionine; Masn=L-alpha-methylasparagine; Mpro=L-alpha-methylproline; Mgln=L-alpha-methylglutamine; Marg=L-alpha-methylarginine; Mser=L-a-methylserine; Mthr=L-alpha-methylthreonine; Mval=L-a-methylvaline; Mtrp=L-alpha-methyltryptophan; Mtyr=L-a-methyltyrosine; Mom=L-alpha-methylornithine; Mnle=L-a-methylnorleucine; amino-alpha-methylbutyric acid; Mnva=L-a-methylnorvaiine; Mhphe=L-alpha-methylhomophenylalanine; Metg=L-a-methylethylglycine; methyl-gamma-aminobutyric acid; methylaminoisobutyric acid; Mtbug=L-alpha-methyl-t-butylglycine; methylpenicillamine; methyl-alpha-naphthylalanine; methylcyclohexylalanine; methylcyclopentylalanine; Dmala=D-alpha-methylalanine; Dmom=D-alpha-methylornithine; Dmcys=D-alpha-methylcysteine; Dmasp=D-alpha-methylaspartic acid; Dmglu=D-alpha-methylglutamic acid; Dmphe=D-alpha-methylphenylalanine; Dmhis=D-alpha-methylhistidine; Dmile=D-alpha-methylisoleucine; Dmlys=D-alpha-methyllysine; Dmleu=D-alpha-methylleucine; Dmmet=D-alpha-methylmethionine; Dmasn=D-alpha-methylasparagine; Dmpro=D-alpha-methylproline; Dmgln=D-alpha-methylglutamine; Dmarg=D-alpha-methylarginine; Dmser=D-alpha-methylserine; Dmthr=D-alpha-methylthreopine; Dmvai=D-alpha-methylvaline; Dmtrp=D-alpha-methyltryptophan; Dmtyr=D-alpha-methyltyrosine; Nmala=L-N-methylalanine; Nmcys=L-N-methyl cysteine; Nmasp=L-N-methylaspartic acid; Nmglu=L-N-methylglutamic acid; Nmphe=L-N-methylphenylalanine; Nmhis=L-N-methylhistidine; Nmile=L-N-methylisoleucine; Nmlys=L-N-methyllysine; Nmleu=L-N-methylleucine; Nmmet=L-N-methylmethionine; Nmasn=L-N-methylasparagine; Nmchexa=N-methyl cyclohexylalanine; Nmgln=L-N-methylglutamine; Nmarg=L-N-methylarginine; Nmser=L-N-methylserine; Nmthr=L-N-methylthreonine; Nmval=L-N-methylvaline; Nmtrp=L-N-methyltryptophan; Nmtyr=L-N-methyltyrosine; Nmorn=L-N-methylornithine; Nmnle=L-N-methylnorleucine; Nmaabu=N-amino-alpha-methylbutyric acid; Nmnva=L-N-methylnorvaline; Nmhphe=L-N-methylhomophenylalanine; Nmetg=L-N-methylethylglycine; Nmgabu=N-methyl-y-aminobutyric acid; Nmcpen=N-methylcyclopentylalanine; Nmtbug=L-N-methyl-t-butylglycine; Nmpen=N-methylpenicillamine; Nmanap=N-methyl-a-naphthylalanine; Nmaib=N-methylaminoisobutyric acid; Naeg=N-(2-aminoethyl)glycine; Dnmala=D-N-methylalanine; Dnmorn=D-N-methylornithine; Dnmcys=D-N-methylcysteine; Dnmasp=D-N-methylaspartic acid; Dmmglu=D-N-methylglutamic acid; Dnmphe=D-N-methylphenylalanine; Dnmhis=D-N-methylhistidine; Dnmile=D-N-methylisoleucine; Dnmlys=D-N-methyllysine; Dnmleu=D-N-methylleucine; Dnmmet=D-N-methylmethionine; Dnmasn=D-N-methylasparagine; Dnmpro=D-N-methylproline; Dnmgln=D-N-methylglutamine; Dnmiarg=D-N-methylarginine; Dmmser=D-N-methylserine; Dmmthr=D-N-methylthreonine; Dnmval=D-N-methylvaline; Dnmtrp=D-N-methyltryptophan; Dnmtyr=D-N-methyltyrosine; Nala=N-methylglycine (sarcosine); Nasp=N-(carboxymethyl)glycine; Nglu=N-(2-carboxyethyl)glycine; Nphe=N-benzylglycine; Nhhis=N-(imidazolylethyl)glycine; Nile=N-(1-methylpropyl)glycine; Nlys=N-(4-aminobutyl)glycine; Nleu=N-(2-methyylpropyl)glycine; Nmet=N-(2-methylthioethyl)glycine; Nhser=N-(hydroxyethyl)glycine; Nasn=N-(carbamylmethyl)glycine; NgIn=N-(2-carbamylethyl)glycine; Nval=N-(1-methylethyl)glycine; Narg=N-(3-guanidinopropyl)glycine; Nhtrp=N-(3-indolylethyl)glycine; Nhtyr=N-(p-hydroxyphenethyl)glycine; Nthr=N-(1-hydroxyethyl)glycine; Ncys=N-(thiomethyl)glycine; Norn=N-(3-aminopropyl)glycine; Ncpro=N-cyclopropylglycine; Ncbut=N-cyclobutyglycine; Nchex=N-cyclohexylglycine; Nchep=N-cycloheptylglycine; Ncoct=N-cyclooctylglycine; Ncdec=N-cyclodecylglycine; Ncund=N-cycloundecylglycine; Ncdod=N-cyclododecyl glycine; Nbhm=N-(2,2-diphenylethyl)glycine; Nbhe=N-(3,3-diphenylpropyl)glycine; Nnbhm=N-(N-(2,2-diphenylethyl)carbamylmethyl)glycine; Nnbhe=N-(N-(3,3-diphenylpropyl)carbamylmethyl)glycine; and Nbmc=1-carboxy-1-(2,2-diphenylethylamino)cyclopropane.

One skilled in the art, using the sequences disclosed herein, can easily synthesize the polypeptides of this invention. Standard procedures for preparing synthetic polypeptides are well known in the art. The novel polypeptides can be synthesized using: the solid phase peptide synthesis (SPPS) method of Merrifield (J. Am. Chem. Soc., 85:2149 (1964)) or modifications of SPPS; or, the polypeptides can be synthesized using standard solution methods well known in the art (see, for example, Bodanzsky, M., Principles of Peptide Synthesis, 2nd revised ed., Springer-Verlag (1988 and 1993)). Alternatively, simultaneous multiple peptide synthesis (SMPS) techniques well known in the art can be used. Polypeptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985).

Within certain aspects of the present invention, one or more novel polypeptides capable of modulating ASARM-peptide and/or PHEX activity herein may be present within a pharmaceutical composition. A pharmaceutical composition comprises one or more ASARM modulating agents in combination with one or more pharmaceutically or physiologically acceptable carriers, diluents, or excipients. Compositions of the present invention may be formulated for any appropriate manner of administration, including for example, topical, oral, nasal, intravenous, intracranial, intraperitoneal, subcutaneous, or intramuscular administration.

Within related aspects, the present invention provides an ASARM modulating agent comprising a polypeptide having the zinc binding domain of PHEX and capable of binding to either the free ASARM peptide or ASARM in full-length MEPE. Also, the present invention provides a PHEX protein activity promoting agent by competing with PHEX for PHEX ligand and/or substrate. In a preferred embodiment, the ASARM-peptide and PHEX protein modulating agent comprises a polypeptide having the PHEX zinc binding domain and two non-contiguous ASARM binding domains. One ASARM binding domain is located on the amino-side of the PHEX zinc binding domain (the "NH-ASARM binding domain" or "NH-ASARM region") and another ASARM binding domain is located on the carboxy-side of the PHEX zinc binding domain (the "COOH-ASARM binding domain" or "COOH-ASARM region"). The amino acid residues between the functional domains of PHEX are removed such that the domains are non-contiguous.

The PHEX zinc binding domain is linked to the NH-ASARM binding domain and/or the COOH-ASARM binding domain using an optional linker. Typically, the linker is a flexible peptide linker between about 1 to 10 amino acids. The linker does not necessarily participate in but may contribute to the function of the binding domain. Therefore, according to the present invention, the linker domain usually a small group of amino acids that provides a spatial bridge between two of the peptide binding domains.

The polypeptides of the present invention may generally comprise from about 40 to 100 amino acid residues, preferably from about 45 to 60 residues. In a preferred embodiment, together the NH-ASARM binding domain, the PHEX zinc binding domain, and the COOH-ASARM binding domain comprise no more than about 45 to 60 amino acid residues of the naturally occurring PHEX protein.

In still another aspect, the novel peptides of the present invention can be thought of as "recombinant" PHEX peptides. For example, as discussed more fully below, an exemplary peptide (SPR4) of the present invention consists of an NH-ASARM binding domain consisting of the amino acid residues at positions 536 to 546 of the PHEX protein, a PHEX zinc binding domain consisting of the amino acids at positions 565 to 591 of the PHEX protein, and a COOH-ASARM binding domain consisting of the amino acids at positions 641 to 648 of the PHEX protein. The peptides or the present invention are "recombinant" in the sense that they consist of three concatenated fragments or domains of the full-length PHEX protein.

It will be appreciated that polypeptides, which are substantially identical to SPR4, are contemplated by the present invention. Generally, two proteins are substantially identical when the amino acid sequences are at least about 70%, typically at least about 80%, more typically at least about 90%, still more typically 95%, 97%, 98%, or 99% or more identical. The comparison of sequences and determination of percent identity and similarity between two sequences can be accomplished using a mathematical algorithm. (Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H G., eds., Humana Press, New Jersey (1994); Sequence Analysis in Molecular Biology, van Heinje, G., Academic Press (1987); and Sequence Analysis Primer, Gribskov, M. and Devereux, J., eds., M Stockton Press, New York (1991)).

In another aspect, the polypeptides of the present invention have functional domains that are substantially identical to each of the NH-ASARM binding domain, PHEX zinc binding domain, and COOH-ASARM binding domain of SPR4. That is, the polypeptides of the present invention that consist of (1) a NH-ASARM binding domain consisting of the amino acid residues which are 70%, 80%, 90%, 95%, 97%, 98%, or 99% identical to those at positions 536 to 546 of the PHEX protein, attached to (2) a PHEX zinc binding domain consisting of the amino acid residues which are 70%, 80%, 90%, 95%, 97%, 98%, or 99% identical to those at positions 565 to 591 of the PHEX protein, attached to (3) a COOH-ASARM binding domain consisting of the amino acid residues which are 70%, 80%, 90%, 95%, 97%, 98%, or 99% identical to those at positions 641 to 648 of the PHEX protein.

The PHEX Zinc Binding Domain

The "PHEX zinc binding domain" refers to the sequence that exists in naturally occurring PHEX or containing one or more conservative substitutions. The PHEX zinc binding domain may be identified based on sequence homology to known zinc binding domain sequences of PHEX, based on the ability of a polypeptide comprising such a sequence to bind to the ASARM sequence and modulate its function, within a representative assay as described herein.

The "PHEX zinc binding domain" comprises the "core PHEX zinc binding domain" and the "PHEX zinc binding flanker sequences."

The core PHEX zinc binding domain generally comprises about 5 to 12 amino acid residues, and preferably about 10 amino acid residues. The core PHEX zinc binding domain has at least three amino acid residues of the native PHEX zinc binding sequence (HEFTH), but may contain conservative substitutions for the remaining residues. The most preferred conservative substitutions are those from the zinc binding motifs from the M13 (MA clan) of zinc metalloendopeptidases (NEP, ECI, KELL, etc.). The most important residues for zinc sequestration are thought to be at positions 580 (H), 581 (E), and 584 (H) corresponding to the full-length PHEX sequence. See Rowe et al., *Distribution of mutations in the PEX gene in families with X-linked hypophosphatemic rickets (HYP)*, Human Mole. Gen., 6, 539-549 (1997), which is incorporated by reference. Thus, in a preferred embodiment, the core PHEX zinc domain comprises the sequence Xaa1-Xaa2-Xaa3-His-Glu-Xaa4-Xaa5-His-Xaa6-Xaa7, wherein Xaa1 is a hydrophobic amino acid;
Xaa2 is a hydrophobic amino acid;
Xaa3 is a hydrophobic amino acid;
Xaa4 is a hydrophobic amino acid;
Xaa5 is a hydrophilic amino acid;
Xaa6 is a hydrophobic amino acid; and
Xaa7 is an aromatic amino acid.

In a more preferred embodiment, the core PHEX zinc binding domain comprises the sequence Xaa1-Xaa2-Xaa3-His-Glu-Xaa4-Xaa5-His-Xaa6-Xaa7, wherein Xaa1 is a hydrophobic amino acid which is an aliphatic amino acid;
Xaa2 is a hydrophobic amino acid which is an aliphatic amino acid;
Xaa3 is a hydrophobic amino acid which is glycine (G) or an aliphatic amino
Xaa4 is a hydrophobic amino acid;
Xaa5 is a hydrophilic amino acid which is a hydroxylamino acid;
Xaa6 is a hydrophobic amino acid which is glycine (G) or an aliphatic amino
Xaa7 is an aromatic amino acid.

In still a more preferred embodiment, the core PHEX zinc binding domain comprises the sequence Xaa1-Xaa2-Xaa3-His-Glu-Xaa4-Xaa5-His-Xaa6-Xaa7, wherein Xaa1 is a hydrophobic amino acid which is an aliphatic amino acid selected from valine (V) or isoleucine (I);

Xaa2 is a hydrophobic amino acid which is an aliphatic amino acid selected from valine (V), isoleucine (I), or methionine (M);

Xaa3 is a hydrophobic amino acid selected from glycine (G) or an aliphatic amino acid selected from alanine (A);

Xaa4 is a hydrophobic amino acid selected form phenylalanine (F), leucine (L), or isoleucine (I);

Xaa5 is a hydrophilic amino acid which is a hydroxylamino acid selected from threonine (T) or serine (S);

Xaa6 is a hydrophobic amino acid which is glycine (G) or an aliphatic amino acid from alanine (A) or isoleucine (I); and Xaa7 is an aromatic amino acid selected from phenylalanine (F) or tyrosine (Y).

In still a more preferred aspect, the core PHEX zinc binding domain is selected from one of the following sequences:

Xaa1-Xaa2-Xaa3-HEFTH-Xaa6-Xaa7; or

Xaa1-Xaa2-Xaa3-HELTH-Xaa6-Xaa7; and wherein Xaa1, Xaa2, Xaa3, Xaa6, and Xaa7 are defined as above.

In a most preferred aspect, the core PHEX zinc binding domain comprises the sequence IVGHEFTHGF (SEQ. ID NO. 3), which corresponds to the residues 577 to 586 of the full-length PHEX protein.

In another aspect, the PHEX zinc binding domain includes certain PHEX zinc binding flanker sequences that are thought to be important in forming the appropriate three-dimensional structure for binding to the ASARM and/or other PHEX protein ligands or substrates. The PHEX zinc binding flanker amino acids thought to be important include: (I) the non-polar glycine residues at positions 572 and 575; (2) the non-polar or hydrophobic residues at positions 573 and 574; (3) the polar-hydrophobic-basic triad of residues at positions 565-567; (4) acidic residue at position 587; (5) hydrophilic amino acids at positions 588-589; and (6) the basic residue at position 591.

In one aspect, the polypeptides of the present invention have a PHEX zinc binding domain which includes the core PHEX zinc binding domain and a PHEX zinc binding flanker sequence having one or more hydrophobic residues, such as glycine (G) residues, located on the amino-side of the core PHEX zinc binding domain. In particular, the glycine residues at positions 572 and 575, which are conserved in the M13 family MA clan Zn-metalloendopeptidases, are preferably located on the amino-side of the core PHEX zinc binding domain. Further, one or more hydrophobic residues are preferably located between the two glycine residues. Thus, in another aspect, the PHEX zinc binding domain comprises the sequence Xf1-Xf2-Xf3-Xf4-Xf5-Xaa1-Xaa2-Xaa3-His-Glu-Xaa4-Xaa5-His-Xaa6-Xaa7, wherein Xf1, Xf2, Xf3, Xf4 are independently hydrophobic amino acids;

Xf5 is any amino acid; and

Xaa1-7 are defined as above.

In another aspect, the PHEX zinc binding domain comprises the sequence Xf1-Xf2-Xf3-Xf4-Xf5-Xaa1-Xaa2-Xaa3-His-Glu-Xaa4-Xaa5-His-Xaa6-Xaa7, wherein Xf1, Xf2, Xf3, Xf4 are independently hydrophobic amino acids which are glycine (G) or aliphatic amino acids;

Xf5 is a hydrophobic amino acid or a hydroxylamino acid; and

Xaa1-7 are defined as above.

In still another aspect, the PHEX zinc binding domain comprises the sequence Xf1-Xf2-Xf3-Xf4-Xf5-Xaa1-Xaa2-Xaa3-His-Glu-Xaa4-Xaa5-His-Xaa6-Xaa7, wherein Xf1, Xf2, Xf3, Xf4 are independently selected from glycine (G), alanine (A), valine (V), or isoleucine (I);

Xf5 is a hydrophobic amino acid or a hydroxylamino acid selected from valine (V), threonine (T), serine (S), or methionine (M); and Xaa1-7 are defined as above.

In an even more preferred aspect, the PHEX zinc binding domain comprises the acid sequence Xf1-Xf2-Xf3-Xf2-Xf5-Xaa1-Xaa2-Xaa3-His-Glu-Xaa4-Xaa5-His-Xaa6-Xaa7, wherein Xf1 is glycine (G);

Xf2 is glycine (G) or an aliphatic amino acid;

Xf3 is an aliphatic amino acid;

Xf4 is glycine (G);

Xf5 is a hydrophobic amino acid or a hydroxylamino acid; and wherein Xaa1-7 are defined as above.

In an even more preferred embodiment, the PHEX zinc binding domain comprises the sequence GAIGVIVGHEFTHGF (SEQ ID NO. 4), which corresponds to positions 572 to 586 of the full-length PHEX sequence.

In another aspect, the PHEX zinc binding domain includes a PHEX zinc binding flanker sequence comprising a polar-hydrophobic-basic triad amino acid sequence. Most preferably the polar-hydrophobic-basic triad is Tyr-Pro-Arg. Thus, in one embodiment, the PHEX zinc binding domain comprises the sequence Xftri1-Xftri2-Xftri3-Nfaa-Xf1-Xf2-Xf3-Xf4-Xf5-Xaa1-Xaa2-Xaa3-His-Glu-Xaa4-Xaa5-His-Xaa6-Xaa7, wherein Xftri1 is a polar amino acid (preferably tyrosine (Y));

Xftri2 is a hydrophobic amino acid (preferably proline (P));

Xftri3 is a basic amino acid (preferably arginine (R) or lysine (K));

Nfaa is an amino acid linker of about 2 to 7 amino acids;

Xf1, Xf2, Xf3, Xf4, Xf5 are defined above; and

Xaa1, Xaa2, Xaa3, Xaa4, Xaa5, Xlaa6, and Xaa7 are defined above.

In an even more preferred embodiment, Nfaa linker comprises the sequence Nfaa1-Nfaa2-Nfaa3-Nfaa4, wherein Nfaa1 is an aliphatic or hydroxylamino acid;

Nfaa2 is an aliphatic amino acid;

Nfaa3 is a polar amino acid; and

Nfaa4 is an aromatic amino acid.

In still a more preferred embodiment, Nfaa linker comprises the sequence Nfaa1-Nfaa2-Nfaa3-Nfaa4, wherein Nfaa1 is an aliphatic or hydroxylamino acid selected from serine (S) or alanine (A);

Nfaa2 is an aliphatic amino acid selected from leucine (L), valine (V), or isoleucine (I);

Nfaa3 is a polar amino acid selected from asparagine (N) or serine (S); and

Nfaa4 is an aromatic amino acid selected from tyrosine (Y) or phenylalanine (F).

In an exemplary embodiment, the PHEX zinc binding domain comprises the sequence Xftri1-Xftri2-Xftri3-Nfaa-Xf1-Xf2-Xf3-Xf4-Xf5-Xaa1-Xaa2-Xaa3-His-Glu-Xaa4-Xaa5-His-Xaa6-Xaa7, wherein Xftri1 is tyrosine (Y);

Xftri2 is proline (P);

Xftri3 is arginine (R);

Nfaa is the amino acid linker-Ser-Lys-Ser-Tyr-

Xf1 is glycine (G);

Xf2 is alanine (A);

Xf3 is isoleucine (I);

Xf4 is glycine (G);

Xf5 is valine (V);

Xaa1 is isoleucine (I);

Xaa2 is valine (V);

Xaa3 is glycine (G);
Xaa4 is phenylalanine (F);
Xaa5 is threonine (T);
Xaa6 is glycine (G); and
Xaa7 is phenylalanine (F).
or YPRSLSYGAIGVIVGHEFTHGF (SEQ. ID NO. 5), which corresponds to positions 565 to 586 of the full-length PHEX sequence.

In another embodiment, the PHEX zinc binding domain includes a PHEX zinc sequence on the carboxy-side of the core PHEX zinc binding domain. This flanker sequence preferably mimics the highly conserved acidic aspartate at position D587 and the hydrophilic amino acids at positions 588-589 of the PHEX sequence followed by a basic amino acid at position 591. Thus, on the carboxy-side of the core PHEX zinc binding domain, there is preferably a flanker sequence such that the PHEX zinc binding domain comprises the sequence Xaa1-Xaa2-Xaa3-His-Glu-Xaa4-Xaa5-His-Xaa6-Xaa7-Xf6-Xf7-Xf8-X-9-Xf10, wherein Xf6 is a polar amino acid or an acidic amino acid;
Xf7 is an hydrophilic amino acid;
Xf8 is a hydrophilic amino acid; Xf9 is a hydrophobic amino acid;
Xf10 is a basic amino acid; and
Xaa1-7 are defined above.

In a more preferred aspect, the carboxy-side flanker sequence of the PHEX zinc binding domain comprises the sequence Xaa1-Xaa2-Xaa3-His-Glu-Xaa4-Xaa5-His-Xaa6-Xaa7-Xf6-Xf7-Xf8-X-9-Xf10, wherein Xf6 is a aspartic acid (D);
Xf7 is a hydrophilic amino acid selected from asparagine (N), aspartic acid (D), or glutamine (Q);
Xf8 is a hydrophilic amino acid selected from asparagine (N) or glutamine (Q);
Xf9 is a hydrophobic amino acid selected from glycine (G) or an aliphatic amino acid;
Xf10 is a basic amino acid selected from arginine (R); and
Xaa1-7 are defined above.

Thus, in one aspect, the PHEX zinc binding domain comprises the sequence YPRSLSYGAIGVIVGHEFTHGFDN-NGR (SEQ. ID NO. 6) which corresponds to positions 565 to 591 of the full-length PHEX sequence.

ASARM Binding Domains

In addition, to the PHEX zinc binding domain, the polypeptides of the present invention also contain at least two ASARM binding domains. One ASARM binding domain is located on the amino-side of the PHEX zinc binding domain (the "NH-ASARM binding domain" or "NH-ASARM region") and another ASARM binding domain is located on the carboxy-side of the PHEX zinc binding domain (the "COOH-ASARM binding domain" or "COOH-ASARM region"). These ASARM binding domains are preferably comprised of non-contiguous segments of the PHEX protein located on the carboxy and amino sides of the PHEX zinc binding domain.

The NH-ASARM Binding Domain

For the NH-ASARM binding domain, the most important residues for ASARM binding specificity are thought to be positions 538 (N) and 539 (A) of the full-length PHEX sequence. Further, the tyrosine (Y) at position 541 is thought to be important for binding. Thus, in one aspect, the NH-ASARM binding domain comprises the sequence Yaa1-Asn-Ala-Yaa2-Yaa-3-Yaa4, wherein Yaa1, Yaa2, Yaa3, and Yaa4 are independently an amino acid.

In a more preferred aspect, the NH-ASARM binding domain comprises the sequence Yaa1-Asn-Ala-Yaa2-Yaa3-Yaa4, wherein Yaa1 is a hydrophobic amino acid;
Yaa2 is an aromatic amino acid;
Yaa3 is a polar amino acid; and
Yaa4 is a hydrophilic amino acid.

In a more preferred aspect, the NH-ASARM binding domain comprises the sequence Yaa1-Asn-Ala-Yaa2-Yaa3-Yaa4, wherein Yaa1 is a hydrophobic amino acid selected from glycine (G) or an aliphatic amino acid;
Yaa2 is an aromatic amino acid selected from phenylalanine (F) or tyrosine (Y);
Yaa3 is a polar amino acid which is a hydroxylamino acid; and
Yaa4 is a hydrophilic amino acid which is a hydroxylamino acid;

In still a more preferred aspect, the NH-ASARM binding domain comprises the sequence Yaa1-Asn-Ala-Yaa2-Yaa3-Yaa4, wherein Yaa1 is a hydrophobic amino acid selected from glycine (G) or an aliphatic amino acid selected from valine (V), alanine (A), or leucine (L);
Yaa2 is an aromatic amino acid selected from phenylalanine (F) or tyrosine (Y);
Yaa3 is a polar amino acid which is a hydroxylamino acid selected from tyrosine (Y); and
Yaa4 is a hydrophilic amino acid which is a hydroxylamino acid selected from serine (S) or threonine (T).

The NH-ASARM binding domain may optionally include a short linker of 1-7 amino acids. Exemplary linkers include ASTN (SEQ. ID No. 7), PNKN (SEQ. ID No. 8), PTKN (SEQ. ID No. 9), VSDH (SEQ. ID No. 10), and SGRN (SEQ. ID No. 11).

Thus, in an even more preferred aspect, the NH-ASARM binding domain comprises the sequence VNAFYS (SEQ. ID No. 12) or VNAYYS (SEQ. ID No. 13). In still a more preferred aspect, the NH-ASARM binding domain comprises the sequence VNAFYS (SEQ. ID No. 12) or VNAYYS (SEQ. ID No. 13) and a 3 to 6 amino acid linker, such as the linker ASTN. Thus, in a most preferred embodiment, the NH-ASARM binding domain comprises the sequence TVNAFYSASTN (SEQ. ID No. 14), which corresponds to positions 536 to 546 of the full-length PHEX sequence.

The COOH-ASARM Binding Domain

For the COOH-ASARM binding domain, the most important residues for ASARM binding specificity are thought to be positions 642 (E) and 646 (D) of the full-length PHEX sequence. Thus, in one aspect, the COOH-ASARM binding domain includes the sequence Zaa1-Glu-Zaa2-Zaa3-Zaa4-Asp, wherein Zaa1, Zaa2, Zaa3, and Zaa4 are independently an amino acid.

In a more preferred aspect, the COOH-ASARM binding domain includes the sequence Zaa1-Glu-Zaa2-Zaa3-Zaa4-Asp, wherein Zaa1 is a hydrophobic amino acid;
Zaa2 is a hydrophilic amino acid;
Zaa3 is a hydrophobic amino acid; and
Zaa4 a hydrophobic amino acid.

In a more preferred aspect, the COOH-ASARM binding domain includes the sequence Zaa1-Glu-Zaa2-Zaa3-Zaa4-Asp, wherein Zaa1 is a hydrophobic amino acid selected from glycine (G) or an aliphatic amino acid;

Zaa2 is a hydrophilic amino acid selected from asparagine (N) or glutamine (Q);

Zaa3 is a hydrophobic amino acid selected from glycine (G) or an aliphatic amino acid; and Zaa4 is a hydrophobic amino acid selected from glycine (G) or an aliphatic amino acid.

In a more preferred aspect, the COOH-ASARM binding domain includes the sequence Zaa1-Glu-Zaa2-Zaa3-Zaa4-Asp, wherein Zaa1 is a hydrophobic amino acid selected from glycine (G);

Zaa2 is a hydrophilic amino acid selected from asparagine (N);

Zaa3 is a hydrophobic amino acid selected from isoleucine (I), leucine (L), or alanine (A); and Zaa4 is hydrophobic amino acid selected from alanine (A).

In an even more preferred aspect, the COOH-ASARM binding domain comprises the sequence GENIAD (SEQ. ID No. 15) or GNAAD (SEQ. ID No. 16). Thus, in a most preferred aspect the COOH-ASARM binding domain comprises the sequence GENIADNG (SEQ. ID No. 17), which corresponds to positions 641 to 648 of the full-length PHEX sequence.

The techniques for synthesizing the polypeptides are present invention are well known to those skilled in the art, such as chemical synthesis (e.g. solid phase peptide synthesis technique), recombinant DNA methods. Exemplary procedures are disclosed in Tournaire et al., "U.S. Pat. No. 6,559,126" and Doherty et al., "U.S. Pat. No. 6,806,255," which are incorporated by reference.

Evaluation of ASARM Modulating Agent Activity

As noted above, wild-type PHEX binds to free ASARM or ASARM contained within full-length MEPE, preferably within or near the zinc binding domain, exhibiting a protective effect. The ability of the ASARM modulating agents of the present invention that bind to ASARM may generally be evaluated using any binding assay known to those of ordinary skill in the art. For example, a Pharmacia Biosensor machine may be used, as discussed in Jonsson et al., Biotechniques 11:520-27 (1991). A specific example of the technology that measures the interaction of polypeptides with molecules can be found in Williams et al., J. Biol. Chem. 272:8539-8545 (1997). Real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or polypeptide (referred to as the ligand) to the surface of a Biosensor chip, followed by binding of the interacting molecule (referred to as the analyte) to the ligand. Binding to the chip is measured in real-time in arbitrary units of resonance ("RU").

Also, a specific PHEX enzymatic assay using a synthetic fluorogenic-peptide assay can be used as described by Campos et al., *Human recombinant endopeptidase PHEX has a strict S1" specificity for acidic residues and cleaves peptides derived from fibroblast growth factor FGF23 and matrix extracellular phosphoglycoprotein*, Biochem J 373:271-9 (2003) may be employed. The activity is extremely low Kcat/Km=100 and not physiological (normal enzymes are at $10^6$ to $10^8$). SPR4 will likely inhibit PHEX activity due to substrate competition.

Surface plasmon resonance experiments may be carried out using a BIAcore XT Biosensor (Pharmacia Ltd., BIAcore, Uppsala, Sweden). Parallel flow cells of CM 5 sensor chips may be derivatized, using the amine coupling method, with streptavidin (200 μg/ml) in 10 mM Sodium Acetate, pH 4.0, according to the manufacturer's protocol. Approximately 2100-2600 resonance units (RU) of ligand may be immobilized, corresponding to a concentration of about 2.1-2.6 ng/mm². The chips may then coated be with a polypeptide comprising a known ASARM modulating agent of the present invention. Any non-specifically bound polypeptide is removed.

To determine binding, test analytes (e.g., the polypeptides of the present invention) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses.

The ability to modulate a ASARM-mediated function may be evaluated using any of a variety of in vitro assays designed to measure the effect of the polypeptide on a typical ASARM-mediated response. The ability of an agent to modulate ASARM function may generally be evaluated in vitro by assaying the effect on mineralization inhibition. The assay involves using MC3T3 cells, bone marrow stromal cells (BMSC), 2T3 cells and/or primary calvarial osteoblasts. Further, direct in vivo administration of ASARM-peptide and the polypeptide (SPR4 peptide) into normal mice and measurements on ameliorative effects on mineralization and renal phosphate handling can be measure. See also Rowe et al., *MEPE has the properties of an osteoblastic phosphatonin and minhibin*, Bone 34:303-319 (2004).

EXAMPLE 1

Polypeptide Design and Synthesis

In this example, various polypeptides were synthesized based on consideration of the PHEX binding region that incorporates the zinc binding motif (SEQ. ID No. 1; HEFTH) and also other key residues important for catalysis, specificity, zinc sequestration, stabilization of the transition state and identity for the MA clan of M13 metalloendopeptidases as generally discussed in Rowe et al., *Distribution of mutations in the PEX gene in families with X-linked hypophosphataemic rickets (HYP)*, Hum. Mol. Genet. 6.539-549 (1997). Moreover, in order to uniquely retain PHEX specificity residues found conserved in rat, mouse and human PHEX were considered for inclusion in the design in positions optimal for biological binding and specificity. The designed polypeptide was thus a truncated, bioinformatically-engineered and altered molecule, derived from a consideration of defined and minimal biological parameters for retention of substrate specificity and binding.

Bio-molecular modeling using Protein Homology/AnalogY Recognition Engine ("PHYRE") and 3D PSSM (available at http://www.sbg.bio.ic.ac.uk/~phyre/) was used to determine probable structure and optimal folding of this the engineered polypeptides. Protein-Explorer available at http://www.umass.edu/microbio/chime/pe_beta/pe/protexpl/frntdoor.htm) was used to visualize the 3D structure of the polypeptides (generated via PHYRE and 3D PSSM) and to compare to other members of the M13 Zn-metalloendopeptidase family, notably neprilysin and thermolysin (X-ray crystallographic data is available for neprilysin, thermolysin and ECE1; NCBI databases). The Protein-Explorer software enables superimposition and comparison of residues with predicted and known structural regions of interest;

PHYRE and 3D PSSM predicted structures of PHEX were also used in designing best fit for the SPR4 polypeptide to the PHEX substrate catalytic site. Table 1 shows key residues conserved in the MA clan of M13 Zn metalloendopeptidases that are important for substrate, binding, catalysis, stabilization of the transition state. The majority of these residues (encompassing the zinc binding motif) were incorporated into the SPR4 polypeptide. Specific regions between these residues were removed on the basis of conservation between species for PHEX (rat, mouse, human, primate, etc.) and structural requirements for folding of the substrate binding site (as modeled using the indicated software).

TABLE 1

Important residues for zinc sequestration and substrate specificity

| Amino acid | NEP | PEX/PHEX | ECE-1 | KELL |
|---|---|---|---|---|
| Asparagine (N) | 542 | 538 | 549 | 540 |
| Alanine (A) | 543 | 539 | 550 | 541 |
| Histidine (H) | 583 | 580 | 590 | 581 |
| Glutamic acid (E) | 584 | 581 | 591 | 582 |
| Histidine (H) | 587 | 584 | 594 | 585 |
| Glutamic acid (E) | 646 | 642 | 650 | 633 |
| Aspartic acid (D) | 650 | 646 | 654 | 638 |

The following polypeptides were synthesized using conventional synthesis techniques.

```
SPR-1: MEPE RGD peptide
                                      (SEQ. ID NO. 18)
Biotin-Ahx*-GYTDLQERGDNDISPFSGDGQPFKD-OH SPR-2: MEPE RGD Random control
                                      (SEQ. ID NO. 19)
Biotin-Ahx*-SQGKDIFPDPDFGLYGDETRQNDGS-OH SPR-3: PHEX Zinc Binding Region
                                      (SEQ. ID NO. 20)
NH2-GTEYPRSLSYGAIGVIVGHEFTHGFDNNGRKYDKNGNLD-OH SPR-4: PHEX Zinc Binding Doman Plus COOH-ASARM
Binding Domain Plus NH-Binding Domain
                                      (SEQ. ID NO. 21)
NH2-
TVNAFYSASTNYPRSLSYGAIGVIVGHEFTHGFDNNGRGENIADNG-OH SPR-5: PHEX region random
                                      (SEQ. ID NO. 22)
NH2-LKGDHSGGNGNYTGLDYNIPGYFRSTIPFHGEVDKENVAR-OH SPR-6: PHEX Zinc Binding Region
                                      (SEQ. ID NO. 23)
NH2-AIGVIVGHEFTHGFDNNGRK-OH SPR-7: PHEX region random
                                      (SEQ. ID NO. 24)
NH2-GHIDEGGHNRAVITGVFNFK-OH SPR-8: ASARM-PO4 biotin
                                      (SEQ. ID NO. 25)
Biotin-Ahx*-
RDDSSESSDSGS(PO3H2)SS(PO3H2)ES(PO3H2)DGD-OH SPR-9.
                                      (SEQ. ID NO. 26)
Biotin-Ahx*-RDDSSESSDSGSSSESDGD-
OH (ASARM nonphosphorylated biotin)

ASARM.
                                      (SEQ. ID NO. 26)
NH2-RDDSSESSDSGSSSESDGD-OH
(non-phosphorylated ASARM-peptide)

ASARM-PO4.
                                      (SEQ. ID NO. 25)
NH2-RDDSSESSDSGS(PO3H2)SS(PO3H2)ES(PO3H2)DGD-OH
(phosphorylated ASARM-peptide)
*Ahx = 6-aminohexanoic acid.
```

EXAMPLE 2

Bone Marrow Stromal Cell Mineralization

In this example, the polypeptides of Example 1 were tested for their ability to improve mineralization of bone marrow stromal cells.

Cell Culture

Adherent bone marrow stromal cells were cultured to assess the relative osteogenic potential of SPR4 peptide based on a classical approach. The epiphyses of the bones from wild type ("WT") and HYP mice were removed, and whole marrow was flushed from the diaphyses by centrifugation at 11500 rpm for 30 seconds in standard culture medium, which consisted of α-MEM (Mediatech Inc, Herndon Va., USA) supplemented with 10% FBS (Mediatech Inc, Herndon Va., USA), 10 U/ml penicillin/100 ug/ml streptomycin. The supernatant was removed, and the cell pellet was resuspended in fresh standard medium. The resuspended cells were plated in standard 25 cm$^2$ flasks and allowed to grow until confluence. The cells were passaged with 0.25% trypsin and 0.02% EDTA (Sigma Aldrich, Saint Louis, Mo., USA). Cells were plated on 24-well plastic culture plates at a concentration of $10 \times 10^4$ cells/well. Starting 72 hours after seeding (referred to as Day 0) nonadherent cells were discarded, and the medium was changed to one that supports osteoblast differentiation, that is, standard media plus 10 mM B glycerophosphate (Sigma Aldrich, Saint Louis, Mo., USA) and 50 mg/liter ascorbic acid (Sigma Aldrich, Saint Louis, Mo., USA). This mineralizing osteogenic medium was used throughout the rest of the culture period. To evaluate the involvement of SPR4 and ASARM-PO$_4$ in the regulation of osteoblasts mineralization cells were treated during the culture period with either 5 μM ASARM-PO$_4$, or 10 μM SPR4 or both. Untreated cells or treated with 10 μM SPR4 random peptide (SPR5) were used as controls. Experimental conditions were compared to cells grown in absence of Bglycerophosphate and ascorbic acid. The compounds were added to the culture medium at Day 0, and renewed every two days.

Mineralization Assay

Monolayers were washed with PBS and fixed in 10% (v/v) formaldehyde (Fisher Scientific) at room temperature for 15 min. The monolayers were then washed twice with excess dH2O prior to addition of 1 mL of 10 mg/ml AR solution in 0.2% ammonium (pH 6.36) per well. The plates were incubated at room temperature for 45 min. with gentle shaking. After aspiration of the unincorporated dye, the wells were washed six times with 2 mL dH2O while shaking for 5 min. The plates were then left at an angle for 2 min. to facilitate removal of excess water, reaspirated, and then stored at −20° C. prior to dye extraction. For quantification of staining, 500 μL 10% (v/v) acetic acid was added to each well, and the plate was incubated at room temperature for 30 min. with shaking. The monolayer, was then scraped from the plate with a cell scraper and transferred with 10% (v/v) acetic acid to a 1,5-mL microcentrifuge tube. After vortexing for 30 sec., the slurry was heated to exactly 85° C. for 10 min., and transferred to ice for 5 min. The slurry was then centrifuged at 20,000 g for 15 min. and 400 µL of the supernatant was removed to a new 1.5-mL microcentrifuge tube and 150 µL of 10% ammonium hydroxide was added to neutralize the pH at down to 4.1-4.5. 150 µL aliquots of the supernatant were read in triplicate at 450 nm in 96-well format using opaque-walled, transparent-bottomed plates.

Figure 2:
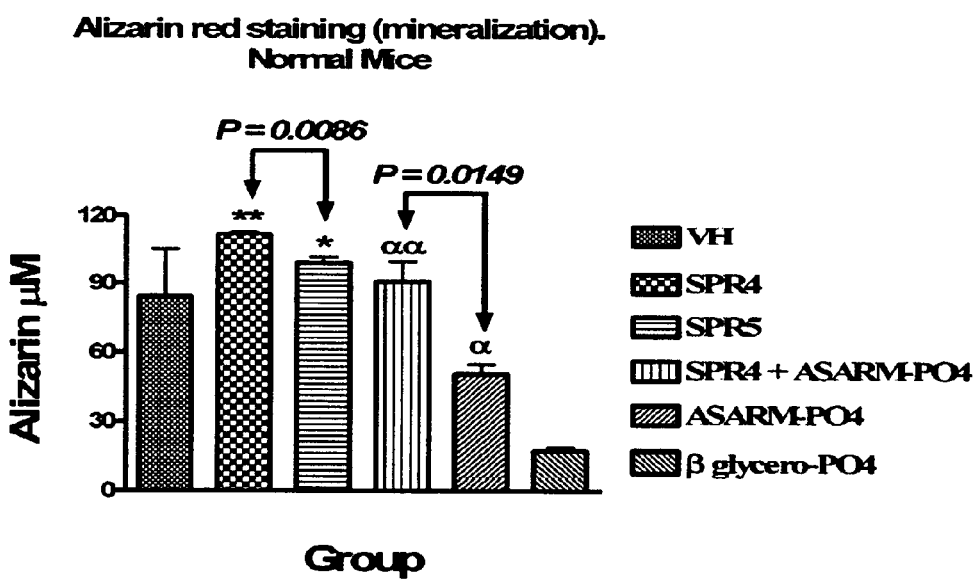
FIG. 2 shows rescue of ASARM-peptide mediated inhibition of mineralization by the SPR4 peptide. Murine bone marrow stromal cell (BMSCs) cultures were stained with alizarin-red in order to quantify the degree of mineralization. The following bars are labeled as: VH, cells supplemented with vehicle; SPR4, cells supplemented with 10 µM SPR4-peptide; SPR5, cells labeled with 10 µM random scrambled control SPR5-peptide; SPR4+ASARM-$PO_4$, cells supplemented with 10 µM SPR4-peptide and 5 µM ASARM-$PO_4$ peptide; and ASARM-$PO_4$, cells supplemented with 5 µM ASARM-$PO_4$ peptide; β-gycero-$PO_4$, cells without phosphate donor (β-gycero-$PO_4$) added to the culture (negative control).
Figure 3:
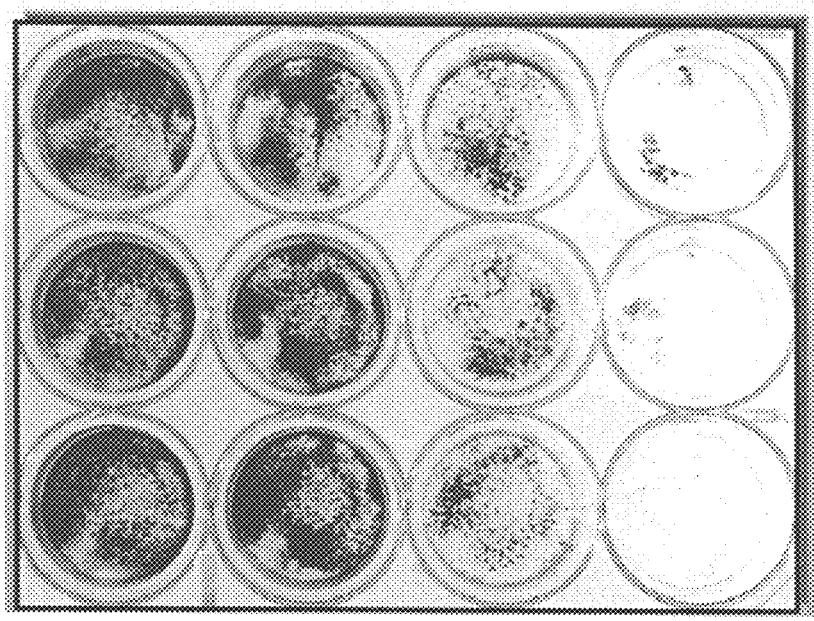
FIG. 3 shows a visual presentation of the alizarin red staining for the experiment described in Example 2.

The results are shown in FIGS. 2 and 3. With vehicle, SPR4 and SPR5 mineralization occurs with great efficiency (elevated alizarin red). With the SPR4 supplemented BMSC cultures, there is a statistically significant improvement in the mineralization (likely due to sequestration of endogenous ASARM-peptides. In cultures supplemented with ASARM-$PO_4$ (5 µM), there is a marked and statistically significant inhibition of mineralization. This is also true for cultures without β-gycero-$PO_4$ donor. In contrast, cultures incubated with SPR4-peptide (10 µM) and ASARM-$PO_4$ peptide (5 µM) in combination have normal mineralization. This confirms that sequestration of ASARM-$PO_4$ by the SPR4 peptide prevents ASARM-$PO_4$ inhibition of mineralization.

EXAMPLE 3

SPR4 forms a Complex with ASARM Peptide that Competes with PHEX

Surface Plasmon Resonance

A Biacore 3000 SPR instrument in conjunction with CM5 research grade chips was used to conduct the surface Plasmon Resonance (SPR) experiments (Biacore, Piscataway, N.J.) as previously described (Rowe et al., Bone 36:33-46 (2005)). The experiments were performed at 25° C. using Biacore buffer (10 mM HEPES pH 7.4, 150 mM NaCl, 0.005% surfactant P20) supplemented with 2 mM $ZnCl_2$ (HBS-P-Zn) or without $ZnCl_2$ (HBS-P) as indicated. Samples were injected at a flow rate of 5 ul/min. The surfaces of research grade CM5 chips were activated by a 6-min. injection of a solution containing 0.2 M N-ethyl-N9-(dimethylaminopropyl) carbodiimide and 0.05 M N-hydroxy-succinimide. Neutravidin (Pierce) was then immobilized on the same chip (ligands) in all four flow-cells using amine coupling chemistry. One neutravidin surface was left blank as a negative control. Biotinylated peptides (including biotinylated ASARM-$PO_4$ peptide) were then added and captured on other individual flow-cells. Biotinylated control peptides SPR1 (MEPE RGD peptide) and SPR2 (MEPE RGD peptide randomized) were captured on the remaining flow-cells (neutravidin binds biotinylated peptides). The experiments were repeated on two different chips and immobilized peptides measured as surface plasmon response units as previously described (Rowe et al., Bone 36:33-46 (2005)). The response unit or RU is a measure of surface charge density oscillation and surface plasmon-positron generation as detected by changes in incident refractive index monitored by the Biacore optical unit. Specifically, 1000 RU equals a change of approximately 1 ng/mm2 in surface protein concentration on the chip surface. Following biotinylated peptide immobilization, PHEX (analyte) was passed over the surfaces for 6 min. at the indicated concentrations in HBS-P-Zn or HBS-P buffer, followed by a 6-min. dissociation. Surfaces were then regenerated by a 1 min. injection of 6 M guanidine-HCl. Protein-protein interactions between analyte (PHEX) and immobilized ligand (biotinylated peptides) are reported as sensorgrams which are plots of RU versus time. An increase in RU reflects changes in the concentration of molecules at the surface of the sensor chip as a result of a specific interaction between analyte and ligand.

Surface Plasmon Resonance: Synthetic Peptides and Competitive PHEX-ASARM-$PO_4$ Binding Studies.

For these experiments, CM-5 chips containing flow cells immobilized with neutravidin captured biotinylated peptides (including Biotinylated ASARM-$PO_4$) were used. Just prior to injection, a stock solution of specific peptide (either SPR3, SPR4, or SPR5) dissolved in analyte buffer (HBS-P-Zn), were added to a constant 50 nM PHEX analyte solution to give final peptide concentrations of either 0, 1.5, 3, 6, 12.5, 25, or 50 µM. In this way, a dose-dependent inhibition curve was calculated for each of the peptides (see Rowe et al., Bone 36:33-46 (2005)). The SPR4 peptide only dose dependently inhibited the binding of analyte PHEX to immobilized biotinylated ASARM-$PO_4$ peptide.

Figure 4A:
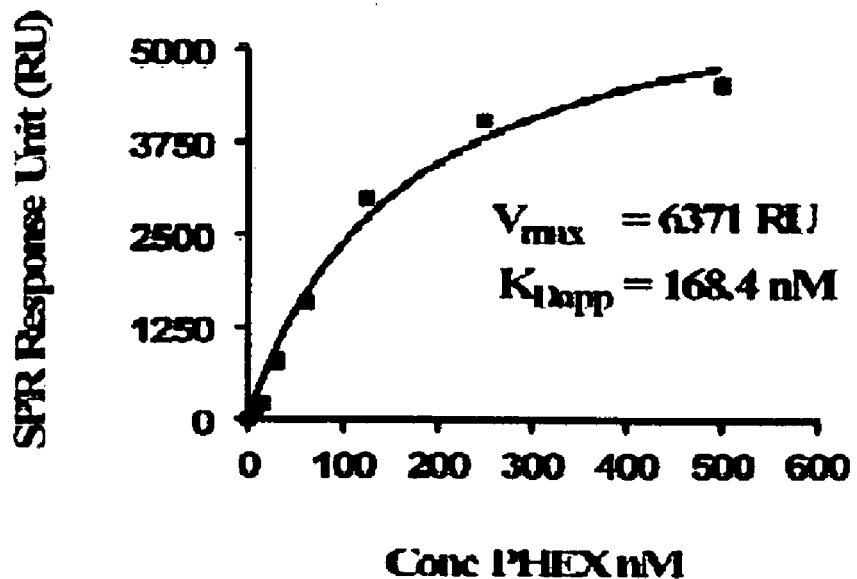
FIGS. 4A and B illustrate the results of surface plasmon resonance experiments in which HEX binds directly to ASARM-$PO_4$.
Figure 4B:
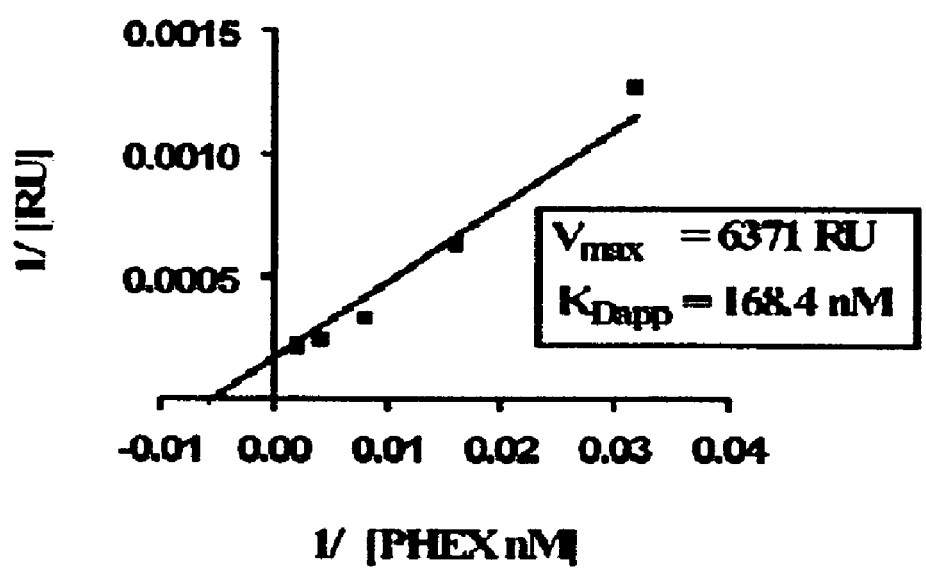
Figure 5A:
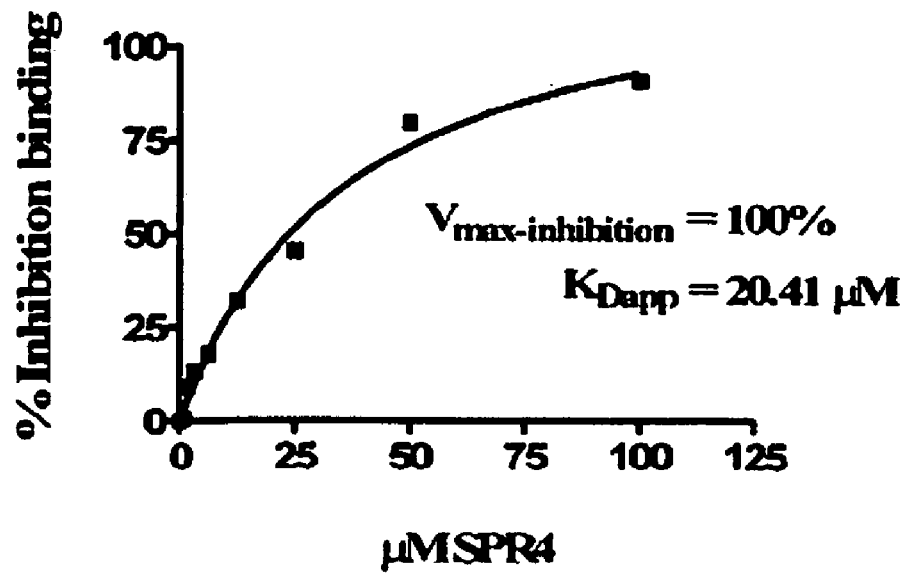
FIGS. 5A and B show the results of surface plasmon resonance experiments in which the SP4 competed with PHEX ASARM-$PO_4$ binding.
Figure 5B:
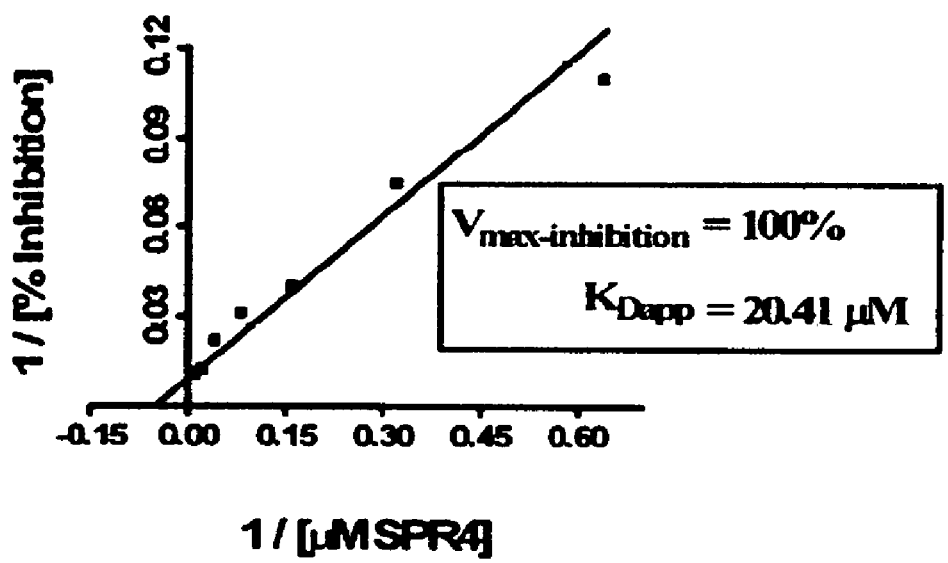

FIG. 4 shows that immobilization of a biotinylated-ASARM-$PO_4$ peptide on a Biacore neutravidin (surface plasmon resonance) chip binds free soluble-PHEX analyte peptide (PHEX at 50 nM). The kinetics of binding is shown in FIG. 4(A) (168.4 nM). FIG. 5 shows that addition of SPR4 to the PHEX analyte (50 nM) at differing concentrations dose-dependently inhibits the ASARM-$PO_4$-PHEX binding. The kinetics of SPR4 competitive-inhibition of ASARM-$PO_4$-PHEX binding is shown in FIG. 5 ($K_{Dapp}$ 20.41 µM with 100% maximal inhibition).

EXAMPLE 4

2D H1/N15 NMR Data

In this example, the 2D H1/N15 NMR experiments were performed in order to confirm the binding of SPR4 to the ASARM polypeptide. All NMR experiments used the a synthetic SPR 4 peptide with N15 isotope was incorporated into targeted "amides" in alanine (6) and glycine (4) residues. The last glycine on the carboxy end of SPR4, however, was not isotopically labelled.

Sample Preparation

All SPR4 samples were made by dissolving 1 mg lyophilized powder in 100 ul of 25 mM acetic acid, pH 3.5 and heating to 37° C. for 15 min., after which time 400 ul 50 mM tris, pH 7 (+/−25 uM $ZnCl_2$) was added. Addition of peptides was accomplished by dissolving the lyophilized powder in the SPR4 containing buffer solution. All samples were incubated at 25° C. for at least 1 hour prior to NMR analysis. 100 mM $CaCl_2$ stock was added to the SPR4+6× ASARM-3$PO_4$ sample to generate a final concentration of 6 mM.

NMR Spectroscopy

Samples were transferred to 5 mM standard $D_2O$ matched NMR tubes (Shigemi) for insertion in to the spectrometer. The $^{15}$N-HSQC experiments were carried out on an 800 MHz Bruker Avance NMR spectrometer with a cryogenically cooled triple-axis probe capable of delivering gradient pulses, utilizing a pulse sequence containing WATERGATE for solvent suppression and sensitivity improvement. All experiments were performed at 25° C. Each data collected using 8 scans with 1024 points in $^1H$ and 128* points in $^{15}N$. The data was processed in nmrPipe using linear prediction with twice the number of collected data points and zero filling to 1600 points. All contour plots were generated at 2.5:1 S/N using Sparky.

Results

Figure 6:
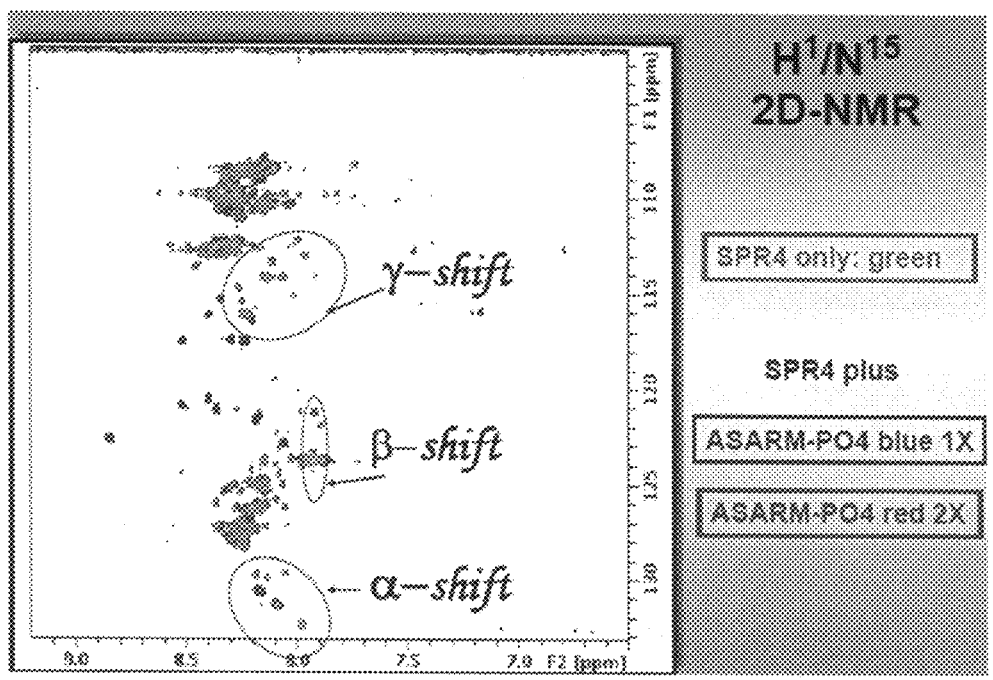
FIG. 6 shows NMR shifts induced by SPR4 plus 1× ASARM and 2× ASARM molar equivalents in solution. There are three spectra superimposed over each other and for clarity the spectra are colored as follows: SPR4 NMR (green); SPR4 plus ASARM-$PO_4$ 1× (blue); and SPR4 plus ASARM-$PO_4$ 2× (red).

FIG. 6 shows NMR shifts (specifically for SPR4) induced by 1×ASARM and 2×ASARM molar equivalents in solution. There are three spectra superimposed over each other and for clarity the spectra are colored as follows: SPR4 NMR (green); SPR4 plus ASARM-PO$_4$ 1× (blue); and SPR4 plus ASARM-PO$_4$ 2× (red).

There are major changes in the SPR4 NMR spectrum (only the SPR4 spectrum is visible, radiolabeled with N15). Three areas highlighted areas are denoted with ellipses. These regions are labeled as alpha, beta, and gamma shifts. In each region, one can clearly see the spectral shift from green to blue to red after addition of ASARM-PO$_4$ peptide. There are also a number of major changes in the 9-8.5 ppm/125-115 ppm region of the 2D H1/N15 matrix. This shows an unequivocal interaction between SPR4 and ASARM-PO$_4$.

Figure 7:
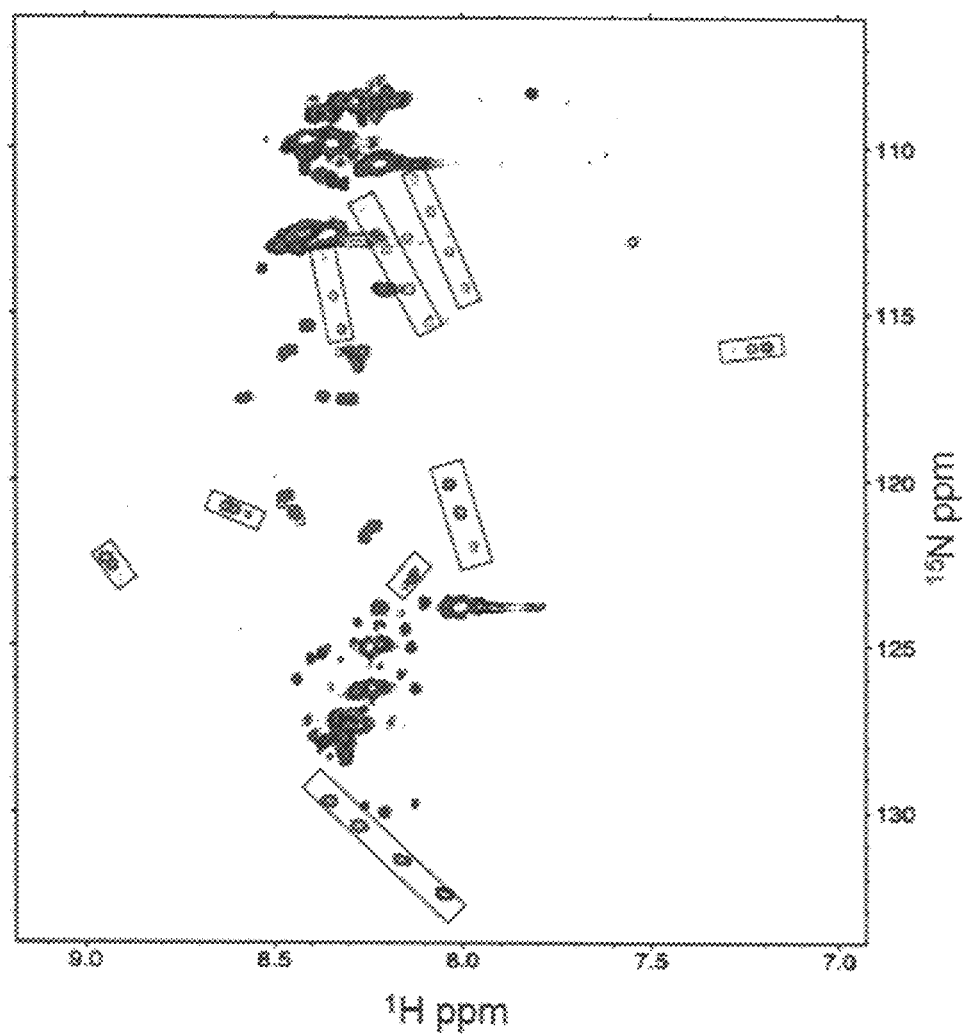
FIG. 7 shows the NMR shifts induced by SPR4 plus 1×, 3×, and 6× ASARM-$PO_4$ molar equivalents: SPR4+Zn (black); SPR4+1× ASARM (red); SPR4+3× ASARM (blue); SPR4+6× ASARM (purple).

FIG. 7 illustrates shifts that results after 1×, 3× and 6× molar equivalents of ASARM-PO$_4$ added to the SPR4 synthetic-peptide. In each sample, the signal still comes from the random coil conformation of SPR4 (unbound state). Peaks in black boxes shift because of binding to ASARM-PO$_4$ and reflect a change in the average conformation of SPR4, which is the sum of bound and unbound states. Black spectrum is SPR4+Zn, Red Spectrum is SPR4+1×ASARM-PO$_4$, Blue Spectrum is SPR4+3×ASARM-PO$_4$, and Purple spectrum is SPR4+6×ASARM-PO$_4$. All spectra were taken in the presence of Zn.

Figure 8:
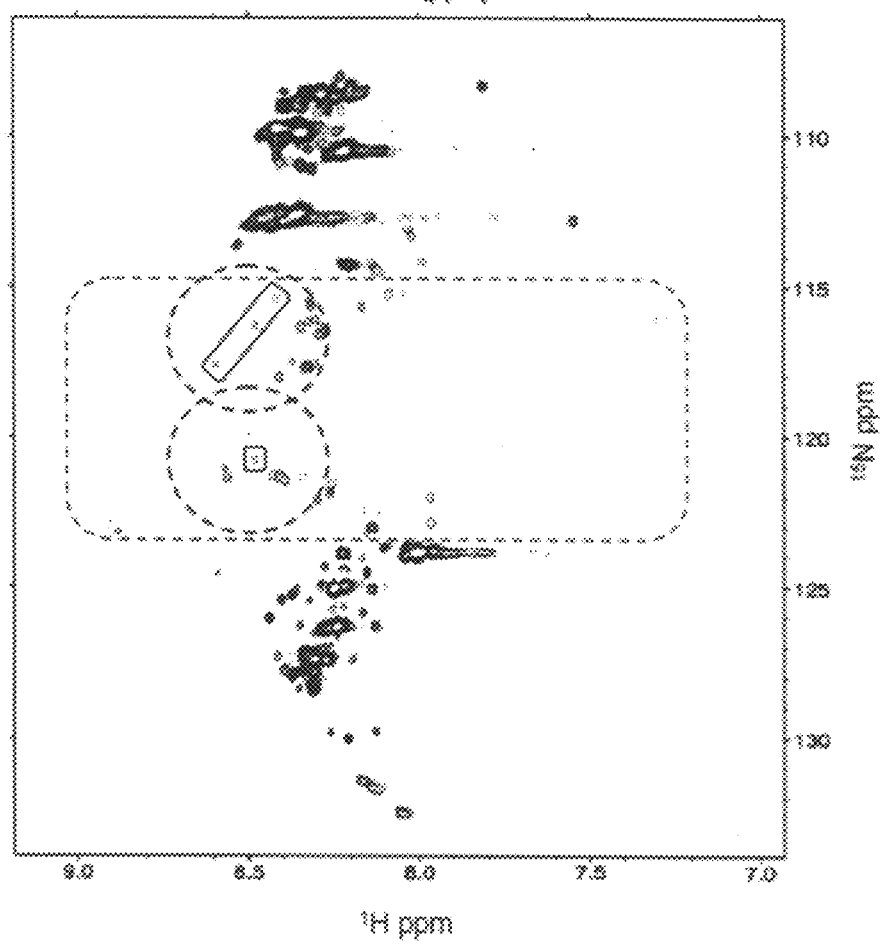
FIG. 8 shows NMR shifts induced by SPR4 with phosphorylated or unphosphorylated ASARM. Black spectrum is of SPR4+Zn; Blue spectrum is of SPR4+1× ASARM-+Zn; and Red spectrum is of SPR4+1× ASARM-3$PO_4$+Zn.

Similar experiments were also performed in order to determine whether SPR4 bound to non-phosphorylated ASARM. Although SPR4 did bind to non-phosphorylated ASARM, differentiation was made between the PO$_4$ component of the ASARM-PO$_4$ interaction. FIG. 8 shows that many chemical shift perturbations occurred as a result of interactions between SPR4 peptide and the ASARM peptide. However, unique chemical shifts appeared when the ASARM was phosphorylated. Solid red boxes enclose peaks unique to the phosphorylated peptide and reflect changes in SPR4 that are specific to interactions with the phosphate moiety. The results indicate that peptide-peptide interactions between SPR4 and ASARM largely determine the bound conformation, whereas the phosphate moieties stabilize the interaction, increasing the binding strength.

From the foregoing it will be seen that this invention is one well adapted to attain all ends and objectives herein-above set forth, together with the other advantages which are obvious and which are inherent to the invention. Further, Since many possible embodiments may be made of the invention without departing from the scope thereof, it is to be understood that all matters herein set forth are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. An isolated polypeptide in which the sequence is at least 80% identical to TVNAFYSASTNYPRSLSYGA-IGVIVGHEFTHGFDNNGRGENIADNG (SEQ. ID NO. 21) ("SPR4").

2. The isolated polypeptide of claim 1 which is 98% identical to SPR4.

3. The isolated polypeptide of claim 1 which is 95% identical to SPR4.

4. The isolated polypeptide of claim 1 which is 90% identical to SPR4.

5. The isolated polypeptide of claim 1 which is 100% identical to SPR4.

* * * * *

```
                        SEQUENCE LISTING

<160> NUMBER OF SEQ ID NOS: 37

<210> SEQ ID NO 1
<211> LENGTH: 5
<212> TYPE: PRT
<213> ORGANISM: Homo sapiens
<220> FEATURE:
<221> NAME/KEY: METAL
<222> LOCATION: (1)..(5)
<223> OTHER INFORMATION: Zinc Binding Motif of PHEX (Residues 580-584)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (580)..(584)

<400> SEQUENCE: 1

His Glu Phe Thr His
1               5

<210> SEQ ID NO 2
<211> LENGTH: 16
<212> TYPE: PRT
<213> ORGANISM: Homo sapiens
<220> FEATURE:
<221> NAME/KEY: BINDING
<222> LOCATION: (1)..(16)
<223> OTHER INFORMATION: ASARM Sequence of MEPE

<400> SEQUENCE: 2

Asp Asp Ser Ser Glu Ser Ser Asp Ser Gly Ser Ser Ser Glu Ser Asp
1               5                   10                  15
```

```
<210> SEQ ID NO 3
<211> LENGTH: 10
<212> TYPE: PRT
<213> ORGANISM: Homo sapiens
<220> FEATURE:
<221> NAME/KEY: METAL
<222> LOCATION: (1)..(10)
<223> OTHER INFORMATION: Core Zinc Binding Domain of PHEX
      (Residues 577-586)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (577)..(586)

<400> SEQUENCE: 3

Ile Val Gly His Glu Phe Thr His Gly Phe
1               5                   10

<210> SEQ ID NO 4
<211> LENGTH: 15
<212> TYPE: PRT
<213> ORGANISM: Homo sapiens
<220> FEATURE:
<221> NAME/KEY: METAL
<222> LOCATION: (1)..(15)
<223> OTHER INFORMATION: Core Zinc Binding Domain of PHEX with Flanker
      Sequences (Residues 572-586)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (572)..(586)

<400> SEQUENCE: 4

Gly Ala Ile Gly Val Ile Val Gly His Glu Phe Thr His Gly Phe
1               5                   10                  15

<210> SEQ ID NO 5
<211> LENGTH: 22
<212> TYPE: PRT
<213> ORGANISM: Homo sapiens
<220> FEATURE:
<221> NAME/KEY: METAL
<222> LOCATION: (1)..(22)
<223> OTHER INFORMATION: Core Zinc Binding Domain of PHEX with Flanker
      Sequences (Residues 565-586)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (565)..(586)

<400> SEQUENCE: 5

Tyr Pro Arg Ser Leu Ser Tyr Gly Ala Ile Gly Val Ile Val Gly His
1               5                   10                  15

Glu Phe Thr His Gly Phe
```

```
<210> SEQ ID NO 6
<211> LENGTH: 27
<212> TYPE: PRT
<213> ORGANISM: Homo sapiens
<220> FEATURE:
<221> NAME/KEY: METAL
<222> LOCATION: (1)..(27)
<223> OTHER INFORMATION: Core Zinc Binding Domain of PHEX with Flanker
      Sequences (Residues 565-591)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (565)..(591)

<400> SEQUENCE: 6

Tyr Pro Arg Ser Leu Ser Tyr Gly Ala Ile Gly Val Ile Val Gly His
1               5                   10                  15

Glu Phe Thr His Gly Phe Asp Asn Asn Gly Arg
            20                  25

<210> SEQ ID NO 7
<211> LENGTH: 4
<212> TYPE: PRT
<213> ORGANISM: Homo sapiens

<400> SEQUENCE: 7

Ala Ser Thr Asn
1

<210> SEQ ID NO 8
<211> LENGTH: 4
<212> TYPE: PRT
<213> ORGANISM: Homo sapiens

<400> SEQUENCE: 8

Pro Asn Lys Asn
1

<210> SEQ ID NO 9
<211> LENGTH: 4
<212> TYPE: PRT
<213> ORGANISM: Homo sapiens

<400> SEQUENCE: 9

Pro Thr Lys Asn
1

<210> SEQ ID NO 10
<211> LENGTH: 4
<212> TYPE: PRT
<213> ORGANISM: Homo sapiens

<400> SEQUENCE: 10

Val Ser Asp His
1

<210> SEQ ID NO 11
<211> LENGTH: 4
<212> TYPE: PRT
```

```
<213> ORGANISM: Homo sapiens

<400> SEQUENCE: 11

Ser Gly Arg Asn
1

<210> SEQ ID NO 12
<211> LENGTH: 6
<212> TYPE: PRT
<213> ORGANISM: Homo sapiens
<220> FEATURE:
<221> NAME/KEY: DOMAIN
<222> LOCATION: (1)..(6)
<223> OTHER INFORMATION: NH-ASARM Binding Domain of PHEX (Residues
      537-542)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (537)..(542)

<400> SEQUENCE: 12

Val Asn Ala Phe Tyr Ser
1               5

<210> SEQ ID NO 13
<211> LENGTH: 6
<212> TYPE: PRT
<213> ORGANISM: Homo sapiens

<400> SEQUENCE: 13

Val Asn Ala Tyr Tyr Ser
1               5

<210> SEQ ID NO 14
<211> LENGTH: 11
<212> TYPE: PRT
<213> ORGANISM: Homo sapiens
<220> FEATURE:
<221> NAME/KEY: DOMAIN
<222> LOCATION: (1)..(11)
<223> OTHER INFORMATION: NH-ASARM Binding Domain of PHEX with Linker
      (Residues 536-546)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (536)..(546)

<400> SEQUENCE: 14

Thr Val Asn Ala Phe Tyr Ser Ala Ser Thr Asn
1               5                   10

<210> SEQ ID NO 15
<211> LENGTH: 6
<212> TYPE: PRT
<213> ORGANISM: Homo sapiens
<220> FEATURE:
<221> NAME/KEY: DOMAIN
<222> LOCATION: (1)..(6)
<223> OTHER INFORMATION: COOH ASARM Binding Domain of PHEX (Residue
```

```
          641-646)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (641)..(646)

<400> SEQUENCE: 15

Gly Glu Asn Ile Ala Asp
1               5

<210> SEQ ID NO 16
<211> LENGTH: 5
<212> TYPE: PRT
<213> ORGANISM: Homo sapiens

<400> SEQUENCE: 16

Gly Asn Ala Ala Asp
1               5

<210> SEQ ID NO 17
<211> LENGTH: 8
<212> TYPE: PRT
<213> ORGANISM: Homo sapiens
<220> FEATURE:
<221> NAME/KEY: DOMAIN
<222> LOCATION: (1)..(8)
<223> OTHER INFORMATION: COOH ASARM Binding Domain of PHEX (Residues
      641-648)
<300> PUBLICATION INFORMATION:
<301> AUTHORS: Rowe, Peter S. N. et al.
<302> TITLE: Distribution of Mutations in the PEX Gene In Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (641)..(648)

<400> SEQUENCE: 17

Gly Glu Asn Ile Ala Asp Asn Gly
1               5

<210> SEQ ID NO 18
<211> LENGTH: 25
<212> TYPE: PRT
<213> ORGANISM: Homo sapiens
<220> FEATURE:
<221> NAME/KEY: DOMAIN
<222> LOCATION: (1)..(25)
<223> OTHER INFORMATION: MEPE RGD Peptide

<400> SEQUENCE: 18

Gly Tyr Thr Asp Leu Gln Glu Arg Gly Asp Asn Asp Ile Ser Pro Phe
1               5                   10                  15

Ser Gly Asp Gly Gln Pro Phe Lys Asp
            20                  25

<210> SEQ ID NO 19
<211> LENGTH: 25
<212> TYPE: PRT
<213> ORGANISM: Homo sapiens
<220> FEATURE:
<221> NAME/KEY: DOMAIN
```

<222> LOCATION: (1)..(25)
<223> OTHER INFORMATION: MEPE RGD Random Control

<400> SEQUENCE: 19

Ser Gln Gly Lys Asp Ile Phe Pro Asp Pro Asp Phe Gly Leu Tyr Gly
1               5                   10                  15

Asp Glu Thr Arg Gln Asn Asp Gly Ser
            20                  25

<210> SEQ ID NO 20
<211> LENGTH: 39
<212> TYPE: PRT
<213> ORGANISM: Homo sapiens
<220> FEATURE:
<221> NAME/KEY: METAL
<222> LOCATION: (1)..(39)
<223> OTHER INFORMATION: PHEX Zinc Binding Region (Residues 562-600)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (562)..(600)

<400> SEQUENCE: 20

Gly Thr Glu Tyr Pro Arg Ser Leu Ser Tyr Gly Ala Ile Gly Val Ile
1               5                   10                  15

Val Gly His Glu Phe Thr His Gly Phe Asp Asn Asn Gly Arg Lys Tyr
            20                  25                  30

Asp Lys Asn Gly Asn Leu Asp
            35

<210> SEQ ID NO 21
<211> LENGTH: 46
<212> TYPE: PRT
<213> ORGANISM: Homo sapiens
<220> FEATURE:
<221> NAME/KEY: MISC_FEATURE
<223> OTHER INFORMATION: PHEX Zinc Binding Domain Plus COOH-ASARM
      Binding Domain Plus NH-Bdining Domain, SPR4

<400> SEQUENCE: 21

Thr Val Asn Ala Phe Tyr Ser Ala Ser Thr Asn Tyr Pro Arg Ser Leu
1               5                   10                  15

Ser Tyr Gly Ala Ile Gly Val Ile Val Gly His Glu Phe Thr His Gly
            20                  25                  30

Phe Asp Asn Asn Gly Arg Gly Glu Asn Ile Ala Asp Asn Gly
            35                  40                  45

<210> SEQ ID NO 22
<211> LENGTH: 40
<212> TYPE: PRT
<213> ORGANISM: Homo sapiens

<400> SEQUENCE: 22

Leu Lys Gly Asp His Ser Gly Asn Gly Asn Tyr Thr Gly Leu Asp
1               5                   10                  15

Tyr Asn Ile Pro Gly Tyr Phe Arg Ser Thr Ile Pro Phe His Gly Glu
            20                  25                  30

Val Asp Lys Glu Asn Val Ala Arg
            35                  40

```
<210> SEQ ID NO 23
<211> LENGTH: 20
<212> TYPE: PRT
<213> ORGANISM: Homo sapiens
<220> FEATURE:
<221> NAME/KEY: METAL
<222> LOCATION: (1)..(20)
<223> OTHER INFORMATION: PHEX Zinc Binding Region (Residues 573-592)
<300> PUBLICATION INFORMATION:
<301> AUTHORS: Rowe, Peter S. N. et al.
<302> TITLE: Distribution of Mutations in the PEX Gene in Families with
      X-Linked Hypophosphataemic Rickets (HYP)
<303> JOURNAL: Human Molecular Genetics
<304> VOLUME: 6
<305> ISSUE: 4
<306> PAGES: 539-549
<307> DATE: 1997
<313> RELEVANT RESIDUES IN SEQ ID NO: (573)..(592)

<400> SEQUENCE: 23

Ala Ile Gly Val Ile Val Gly His Glu Phe Thr His Gly Phe Asp Asn
1               5                   10                  15

Asn Gly Arg Lys
            20

<210> SEQ ID NO 24
<211> LENGTH: 20
<212> TYPE: PRT
<213> ORGANISM: Homo sapiens

<400> SEQUENCE: 24

Gly His Ile Asp Glu Gly Gly His Asn Arg Ala Val Ile Thr Gly Val
1               5                   10                  15

Phe Asn Phe Lys
            20

<210> SEQ ID NO 25
<211> LENGTH: 19
<212> TYPE: PRT
<213> ORGANISM: Homo sapiens
<220> FEATURE:
<221> NAME/KEY: PHOSPHORYLATION
<222> LOCATION: (12)..(12)
<223> OTHER INFORMATION: ASARM-PO4
<220> FEATURE:
<221> NAME/KEY: PHOSPHORYLATION
<222> LOCATION: (14)..(14)
<223> OTHER INFORMATION: ASAM-PO4
<220> FEATURE:
<221> NAME/KEY: PHOSPHORYLATION
<222> LOCATION: (16)..(16)
<223> OTHER INFORMATION: ASARM-PO4

<400> SEQUENCE: 25

Arg Asp Asp Ser Ser Glu Ser Ser Asp Ser Gly Ser Ser Ser Glu Ser
1               5                   10                  15

Asp Gly Asp

<210> SEQ ID NO 26
<211> LENGTH: 19
<212> TYPE: PRT
<213> ORGANISM: Homo sapiens
<220> FEATURE:
<221> NAME/KEY: BINDING
<222> LOCATION: (1)..(19)
<223> OTHER INFORMATION: Non-Phosphorylated ASARM Peptide

<400> SEQUENCE: 26
```

```
Arg Asp Asp Ser Ser Glu Ser Ser Asp Ser Gly Ser Ser Ser Glu Ser
1               5                   10                  15

Asp Gly Asp

<210> SEQ ID NO 27
<211> LENGTH: 6
<212> TYPE: PRT
<213> ORGANISM: Homo sapiens
<220> FEATURE:
<221> NAME/KEY: BINDING
<222> LOCATION: (1)..(6)
<223> OTHER INFORMATION: A Non-Contiguous NH-ASARM Binding Doman
<220> FEATURE:
<221> NAME/KEY: MISC_FEATURE
<222> LOCATION: (1)..(1)
<223> OTHER INFORMATION: X is any amino acid
<220> FEATURE:
<221> NAME/KEY: MISC_FEATURE
<222> LOCATION: (4)..(6)
<223> OTHER INFORMATION: X is any amino acid

<400> SEQUENCE: 27

Xaa Asn Ala Xaa Xaa Xaa
1               5

<210> SEQ ID NO 28
<211> LENGTH: 10
<212> TYPE: PRT
<213> ORGANISM: Homo sapiens
<220> FEATURE:
<221> NAME/KEY: BINDING
<222> LOCATION: (1)..(10)
<223> OTHER INFORMATION: A PHEX Zinc Binding Doman
<220> FEATURE:
<221> NAME/KEY: MISC_FEATURE
<222> LOCATION: (1)..(3)
<223> OTHER INFORMATION: X is a hydrophobic amino acid
<220> FEATURE:
<221> NAME/KEY: MISC_FEATURE
<222> LOCATION: (6)..(7)
<223> OTHER INFORMATION: X is a hydrophobic amino acid
<220> FEATURE:
<221> NAME/KEY: MISC_FEATURE
<222> LOCATION: (9)..(9)
<223> OTHER INFORMATION: X is a hydrophobic amino acid
<220> FEATURE:
<221> NAME/KEY: MISC_FEATURE
<222> LOCATION: (10)..(10)
<223> OTHER INFORMATION: X is a aromatic amino acid

<400> SEQUENCE: 28

Xaa Xaa Xaa His Glu Xaa Xaa His Xaa Xaa
1               5                   10

<210> SEQ ID NO 29
<211> LENGTH: 6
<212> TYPE: PRT
<213> ORGANISM: Homo sapiens
<220> FEATURE:
<221> NAME/KEY: BINDING
<222> LOCATION: (1)..(6)
<223> OTHER INFORMATION: Non-Contiguous COOH-ASARM binding domain
<220> FEATURE:
<221> NAME/KEY: MISC_FEATURE
<222> LOCATION: (1)..(1)
<223> OTHER INFORMATION: X is any amino acid
<220> FEATURE:
<221> NAME/KEY: MISC_FEATURE
<222> LOCATION: (3)..(5)
<223> OTHER INFORMATION: X is any amino acid

<400> SEQUENCE: 29
```

```
Xaa Glu Xaa Xaa Xaa Asp
1               5
```

```
<210> SEQ ID NO 30
<211> LENGTH: 10
<212> TYPE: PRT
<213> ORGANISM: Homo sapiens
<220> FEATURE:
<221> NAME/KEY: BINDING
<222> LOCATION: (1)..(10)
<223> OTHER INFORMATION: A PHEX zinc binding domain
<220> FEATURE:
<221> NAME/KEY: MISC_FEATURE
<222> LOCATION: (1)..(1)
<223> OTHER INFORMATION: X is a hydrophobic amino acid which is an
      aliphatic amino acid selected from valine (V) or isoleucine (I)
<220> FEATURE:
<221> NAME/KEY: MISC_FEATURE
<222> LOCATION: (2)..(2)
<223> OTHER INFORMATION: X is a hydrophobic amino acid which is an
      aliphatic amino acid selected from valine (V) or isoleucine (I) or
      methionine (M)
<220> FEATURE:
<221> NAME/KEY: MISC_FEATURE
<222> LOCATION: (3)..(3)
<223> OTHER INFORMATION: X is a hydrophobic amino acid is glycine (G) or
      an aliphatic amino acid
<220> FEATURE:
<221> NAME/KEY: MISC_FEATURE
<222> LOCATION: (6)..(6)
<223> OTHER INFORMATION: X is a hydrophobic amino acid selected from
      phenylalanine (F), leucine(L) or isoleucine (I)
<220> FEATURE:
<221> NAME/KEY: MISC_FEATURE
<222> LOCATION: (7)..(7)
<223> OTHER INFORMATION: X is a hydrophilic amino acid selected from
      threonine (T)
<220> FEATURE:
<221> NAME/KEY: MISC_FEATURE
<222> LOCATION: (9)..(9)
<223> OTHER INFORMATION: X is a hydrophobic amino acid is glycine (G) or
      an aliphatic amino acid selected from alanine (A) or isoleucine
      (I)
<220> FEATURE:
<221> NAME/KEY: MISC_FEATURE
<222> LOCATION: (10)..(10)
<223> OTHER INFORMATION: X is an aromatic amino acid selected from
      phenylalanine (F) or tyrosine (Y)

<400> SEQUENCE: 30

Xaa Xaa Xaa His Glu Xaa Xaa His Xaa Xaa
1               5                   10

<210> SEQ ID NO 31
<211> LENGTH: 15
<212> TYPE: PRT
<213> ORGANISM: Homo sapiens
<220> FEATURE:
<221> NAME/KEY: BINDING
<222> LOCATION: (1)..(15)
<223> OTHER INFORMATION: A PHEX zinc binding domain
<220> FEATURE:
<221> NAME/KEY: MISC_FEATURE
<222> LOCATION: (1)..(5)
<223> OTHER INFORMATION: Flanker Sequence
<220> FEATURE:
<221> NAME/KEY: MISC_FEATURE
<222> LOCATION: (1)..(4)
<223> OTHER INFORMATION: X are independently hydrophobic amino acids
<220> FEATURE:
<221> NAME/KEY: MISC_FEATURE
<222> LOCATION: (5)..(5)
<223> OTHER INFORMATION: X is any amino acid
<220> FEATURE:
<221> NAME/KEY: MISC_FEATURE
```

```
<222> LOCATION: (6)..(8)
<223> OTHER INFORMATION: X is a hydrophobic amino acid
<220> FEATURE:
<221> NAME/KEY: MISC_FEATURE
<222> LOCATION: (11)..(12)
<223> OTHER INFORMATION: X is a hydrophobic amino acid
<220> FEATURE:
<221> NAME/KEY: MISC_FEATURE
<222> LOCATION: (14)..(14)
<223> OTHER INFORMATION: X is a hydrophobic amino acid
<220> FEATURE:
<221> NAME/KEY: MISC_FEATURE
<222> LOCATION: (15)..(15)
<223> OTHER INFORMATION: X is an aromatic amino acid

<400> SEQUENCE: 31

Xaa Xaa Xaa Xaa Xaa Xaa Xaa Xaa His Glu Xaa Xaa His Xaa Xaa
1               5                   10                  15

<210> SEQ ID NO 32
<211> LENGTH: 25
<212> TYPE: PRT
<213> ORGANISM: Homo sapiens
<220> FEATURE:
<221> NAME/KEY: BINDING
<222> LOCATION: (1)..(19)
<223> OTHER INFORMATION: a PHEX zinc binding domain
<220> FEATURE:
<221> NAME/KEY: MISC_FEATURE
<222> LOCATION: (1)..(3)
<223> OTHER INFORMATION: Flanker Sequence
<220> FEATURE:
<221> NAME/KEY: MISC_FEATURE
<222> LOCATION: (1)..(1)
<223> OTHER INFORMATION: X is a polar amino acid
<220> FEATURE:
<221> NAME/KEY: MISC_FEATURE
<222> LOCATION: (2)..(2)
<223> OTHER INFORMATION: X is a hydrophobic amino acid
<220> FEATURE:
<221> NAME/KEY: MISC_FEATURE
<222> LOCATION: (3)..(3)
<223> OTHER INFORMATION: X is a basic amino acid
<220> FEATURE:
<221> NAME/KEY: MISC_FEATURE
<222> LOCATION: (4)..(10)
<223> OTHER INFORMATION: X is an amino acid linker of about 2 to 7 amino
      acids
<220> FEATURE:
<221> NAME/KEY: MISC_FEATURE
<222> LOCATION: (11)..(14)
<223> OTHER INFORMATION: X are independently hydrophobic amino acids
<220> FEATURE:
<221> NAME/KEY: MISC_FEATURE
<222> LOCATION: (15)..(15)
<223> OTHER INFORMATION: X is any amino acid
<220> FEATURE:
<221> NAME/KEY: MISC_FEATURE
<222> LOCATION: (16)..(18)
<223> OTHER INFORMATION: X is a hydrophobic amino acid
<220> FEATURE:
<221> NAME/KEY: MISC_FEATURE
<222> LOCATION: (21)..(22)
<223> OTHER INFORMATION: X is a hydrophobic amino acid
<220> FEATURE:
<221> NAME/KEY: MISC_FEATURE
<222> LOCATION: (24)..(24)
<223> OTHER INFORMATION: X is a hydrophobic amino acid
<220> FEATURE:
<221> NAME/KEY: MISC_FEATURE
<222> LOCATION: (25)..(25)
<223> OTHER INFORMATION: X is an aromatic amino acid

<400> SEQUENCE: 32

Xaa Xaa Xaa Xaa Xaa Xaa Xaa Xaa Xaa Xaa Xaa Xaa Xaa Xaa Xaa
1               5                   10                  15
```

Xaa Xaa His Glu Xaa Xaa His Xaa Xaa
            20                  25

```
<210> SEQ ID NO 33
<211> LENGTH: 22
<212> TYPE: PRT
<213> ORGANISM: Homo sapiens
<220> FEATURE:
<221> NAME/KEY: BINDING
<222> LOCATION: (1)..(19)
<223> OTHER INFORMATION: A PHEX zinc binding domain
<220> FEATURE:
<221> NAME/KEY: MISC_FEATURE
<222> LOCATION: (1)..(1)
<223> OTHER INFORMATION: X is tyrosine (Y)
<220> FEATURE:
<221> NAME/KEY: MISC_FEATURE
<222> LOCATION: (2)..(2)
<223> OTHER INFORMATION: X is proline (P)
<220> FEATURE:
<221> NAME/KEY: MISC_FEATURE
<222> LOCATION: (3)..(3)
<223> OTHER INFORMATION: X is arginine (R)
<220> FEATURE:
<221> NAME/KEY: MISC_FEATURE
<222> LOCATION: (4)..(7)
<223> OTHER INFORMATION: X is the amino acid linker represented by amino
      acid serine (S) at location 4, leucine (L) at location 5, serine
      (S) at location 6 and tyrosine (Y) at location 7
<220> FEATURE:
<221> NAME/KEY: MISC_FEATURE
<222> LOCATION: (8)..(8)
<223> OTHER INFORMATION: X is glycine (G)
<220> FEATURE:
<221> NAME/KEY: MISC_FEATURE
<222> LOCATION: (9)..(9)
<223> OTHER INFORMATION: X is alanine (A)
<220> FEATURE:
<221> NAME/KEY: MISC_FEATURE
<222> LOCATION: (10)..(10)
<223> OTHER INFORMATION: X is isoleucine (I)
<220> FEATURE:
<221> NAME/KEY: MISC_FEATURE
<222> LOCATION: (11)..(11)
<223> OTHER INFORMATION: X is glycine (G)
<220> FEATURE:
<221> NAME/KEY: MISC_FEATURE
<222> LOCATION: (12)..(12)
<223> OTHER INFORMATION: X is valine (V)
<220> FEATURE:
<221> NAME/KEY: MISC_FEATURE
<222> LOCATION: (13)..(13)
<223> OTHER INFORMATION: X is isoleucine (I)
<220> FEATURE:
<221> NAME/KEY: MISC_FEATURE
<222> LOCATION: (14)..(14)
<223> OTHER INFORMATION: X is valine (V)
<220> FEATURE:
<221> NAME/KEY: MISC_FEATURE
<222> LOCATION: (15)..(15)
<223> OTHER INFORMATION: X is glycine (G)
<220> FEATURE:
<221> NAME/KEY: MISC_FEATURE
<222> LOCATION: (18)..(18)
<223> OTHER INFORMATION: X is phenylalanine (F)
<220> FEATURE:
<221> NAME/KEY: MISC_FEATURE
<222> LOCATION: (19)..(19)
<223> OTHER INFORMATION: X is threonine (T)
<220> FEATURE:
<221> NAME/KEY: MISC_FEATURE
<222> LOCATION: (21)..(21)
<223> OTHER INFORMATION: X is glycine (G)
<220> FEATURE:
<221> NAME/KEY: MISC_FEATURE
<222> LOCATION: (22)..(22)
<223> OTHER INFORMATION: X is phenylalanine (F)
```

<400> SEQUENCE: 33

Xaa Xaa Xaa Xaa Xaa Xaa Xaa Xaa Xaa Xaa Xaa Xaa Xaa Xaa His
1               5                   10                  15

Glu Xaa Xaa His Xaa Xaa
            20

<210> SEQ ID NO 34
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: A PHEX zinc binding domain
<220> FEATURE:
<221> NAME/KEY: MISC_FEATURE
<222> LOCATION: (1)..(3)
<223> OTHER INFORMATION: X is a hydrophobic amino acid
<220> FEATURE:
<221> NAME/KEY: MISC_FEATURE
<222> LOCATION: (6)..(7)
<223> OTHER INFORMATION: X is a hydrophobic amino acid
<220> FEATURE:
<221> NAME/KEY: MISC_FEATURE
<222> LOCATION: (9)..(9)
<223> OTHER INFORMATION: X is a hydrophobic amino acid
<220> FEATURE:
<221> NAME/KEY: MISC_FEATURE
<222> LOCATION: (10)..(10)
<223> OTHER INFORMATION: X is an aromatic amino acid
<220> FEATURE:
<221> NAME/KEY: MISC_FEATURE
<222> LOCATION: (11)..(15)
<223> OTHER INFORMATION: A flanker sequence
<220> FEATURE:
<221> NAME/KEY: MISC_FEATURE
<222> LOCATION: (11)..(11)
<223> OTHER INFORMATION: X is a polar or an acidic amino acid
<220> FEATURE:
<221> NAME/KEY: MISC_FEATURE
<222> LOCATION: (12)..(14)
<223> OTHER INFORMATION: X is a hydrophilic amino acid
<220> FEATURE:
<221> NAME/KEY: MISC_FEATURE
<222> LOCATION: (15)..(15)
<223> OTHER INFORMATION: X is a basic amino acid

<400> SEQUENCE: 34

Xaa Xaa Xaa His Glu Xaa Xaa His Xaa Xaa Xaa Xaa Xaa Xaa Xaa
1               5                   10                  15

<210> SEQ ID NO 35
<211> LENGTH: 6
<212> TYPE: PRT
<213> ORGANISM: Homo sapiens
<220> FEATURE:
<221> NAME/KEY: BINDING
<222> LOCATION: (1)..(6)
<223> OTHER INFORMATION: An NH-ASARM binding domain
<220> FEATURE:
<221> NAME/KEY: MISC_FEATURE
<222> LOCATION: (1)..(1)
<223> OTHER INFORMATION: X is a hydrophobic amino acid
<220> FEATURE:
<221> NAME/KEY: MISC_FEATURE
<222> LOCATION: (4)..(4)
<223> OTHER INFORMATION: X is an aromatic amino acid
<220> FEATURE:
<221> NAME/KEY: MISC_FEATURE
<222> LOCATION: (5)..(5)
<223> OTHER INFORMATION: X is a polar amino acid
<220> FEATURE:
<221> NAME/KEY: MISC_FEATURE

```
<222> LOCATION: (6)..(6)
<223> OTHER INFORMATION: X is a hydrophilic amino acid

<400> SEQUENCE: 35

Xaa Asn Ala Xaa Xaa Xaa
1               5

<210> SEQ ID NO 36
<211> LENGTH: 6
<212> TYPE: PRT
<213> ORGANISM: Homo sapiens
<220> FEATURE:
<221> NAME/KEY: BINDING
<222> LOCATION: (1)..(6)
<223> OTHER INFORMATION: A COOH-ASARM binding domain
<220> FEATURE:
<221> NAME/KEY: MISC_FEATURE
<222> LOCATION: (1)..(1)
<223> OTHER INFORMATION: X is a hydrophobic amino acid
<220> FEATURE:
<221> NAME/KEY: MISC_FEATURE
<222> LOCATION: (3)..(3)
<223> OTHER INFORMATION: X is a hydrophilic amino acid
<220> FEATURE:
<221> NAME/KEY: MISC_FEATURE
<222> LOCATION: (4)..(5)
<223> OTHER INFORMATION: X is a hydrophobic amino acid

<400> SEQUENCE: 36

Xaa Glu Xaa Xaa Xaa Asp
1               5

<210> SEQ ID NO 37
<211> LENGTH: 6
<212> TYPE: PRT
<213> ORGANISM: Homo sapiens
<220> FEATURE:
<221> NAME/KEY: BINDING
<222> LOCATION: (1)..(6)
<223> OTHER INFORMATION: A COOH-ASARM binding domain
<220> FEATURE:
<221> NAME/KEY: MISC_FEATURE
<222> LOCATION: (1)..(1)
<223> OTHER INFORMATION: X is a hydrophobic amino acid selected from
      glycine (G) or an aliphatic amino acid
<220> FEATURE:
<221> NAME/KEY: MISC_FEATURE
<222> LOCATION: (3)..(3)
<223> OTHER INFORMATION: X is a hydrophilic amino acid selected from
      asparagine (N) or glutamine (Q)
<220> FEATURE:
<221> NAME/KEY: MISC_FEATURE
<222> LOCATION: (4)..(5)
<223> OTHER INFORMATION: X is a hydrophobic amino acid selected from
      glycine (G) or an aliphatic amino acid

<400> SEQUENCE: 37

Xaa Glu Xaa Xaa Xaa Asp
1               5
```